United States Patent
Cholette et al.

(10) Patent No.: US 12,201,828 B2
(45) Date of Patent: *Jan. 21, 2025

(54) SYSTEM AND METHODS FOR THERAPEUTIC STIMULATION

(71) Applicant: NeoGenesis Technologies LLC, Houston, TX (US)

(72) Inventors: Martin Cholette, Van Alstyne, TX (US); Gary Dulak, Moorpark, CA (US)

(73) Assignee: NeoGenesis Technologies LLC, Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/458,813

(22) Filed: Aug. 30, 2023

(65) Prior Publication Data

US 2024/0165402 A1    May 23, 2024

Related U.S. Application Data

(63) Continuation of application No. 15/961,751, filed on Apr. 24, 2018, now Pat. No. 11,779,755.
(Continued)

(51) Int. Cl.
| | | |
|---|---|---|
| *A61N 1/05* | (2006.01) | |
| *A61N 1/36* | (2006.01) | |
| *A61N 1/372* | (2006.01) | |

(52) U.S. Cl.
CPC ....... *A61N 1/0551* (2013.01); *A61N 1/36075* (2013.01); *A61N 1/36139* (2013.01);
(Continued)

(58) Field of Classification Search
CPC .............. A61N 1/0551; A61N 1/36062; A61N 1/36071; A61N 1/36132; A61N 1/36171; A61N 1/37235
See application file for complete search history.

(56) References Cited

U.S. PATENT DOCUMENTS

11,779,755 B2 * 10/2023 Cholette ............ A61N 1/36146
607/117
2005/0102006 A1    5/2005 Whitehurst et al.
(Continued)

OTHER PUBLICATIONS

Abbott, L.F. et al., Synaptic Computation, Insight Review Articles, Volumed 431, Nature Publishing Group, Oct. 14, 2004 in 8 pages.
(Continued)

*Primary Examiner* — Rex R Holmes
*Assistant Examiner* — Jennifer L Ghand
(74) *Attorney, Agent, or Firm* — Knobbe Martens Olson & Bear, LLP

(57) ABSTRACT

A system and method for providing electrical stimulation to biological tissue to treat medical conditions. The system can include a lead configured to be positioned in contact with biological tissue proximate one or more occipital nerves, an implantable pulse generator configured to deliver electrical stimulation to the biological tissue via the one or more leads, and/or a power source configured to operatively connect and supply power to the implantable pulse generator. The system can further include a processor configured to communicate with the implantable pulse generator. The processor can operate the implantable pulse generator to deliver the electrical stimulation to the biological tissue via the lead. The implantable pulse generator can deliver the electrical stimulation by applying a stimulation waveform or a stimulation pattern. The stimulation waveform can include a series of stimulation pulses that can vary over time, which can reduce an effect of neural accommodation or adaptation.

22 Claims, 25 Drawing Sheets

Related U.S. Application Data

(60) Provisional application No. 62/489,925, filed on Apr. 25, 2017.

(52) U.S. Cl.
CPC ........ *A61N 1/36146* (2013.01); *A61N 1/0526* (2013.01); *A61N 1/36062* (2017.08); *A61N 1/36071* (2013.01); *A61N 1/36132* (2013.01); *A61N 1/3615* (2013.01); *A61N 1/36171* (2013.01); *A61N 1/36175* (2013.01); *A61N 1/37235* (2013.01)

(56) References Cited

U.S. PATENT DOCUMENTS

| | | |
|---|---|---|
| 2005/0216070 A1 | 9/2005 | Boveja et al. |
| 2006/0004423 A1 | 1/2006 | Boveja et al. |
| 2006/0206165 A1 | 9/2006 | Jaax et al. |
| 2008/0027505 A1 | 1/2008 | Levin et al. |
| 2008/0262566 A1 | 10/2008 | Jaax |
| 2008/0281381 A1 | 11/2008 | Gerber et al. |
| 2009/0076561 A1 | 3/2009 | Libbus et al. |
| 2010/0023090 A1 | 1/2010 | Jaax et al. |
| 2010/0121407 A1 | 5/2010 | Pfaff et al. |
| 2010/0280417 A1 | 11/2010 | Skelton et al. |
| 2011/0184488 A1 | 7/2011 | Ridder |
| 2012/0016437 A1 | 1/2012 | Altaris et al. |
| 2012/0197336 A1 | 8/2012 | Su |
| 2012/0277621 A1 | 11/2012 | Gerber et al. |
| 2013/0289667 A1 | 10/2013 | Wacnik et al. |
| 2015/0217117 A1 | 8/2015 | Hershey |
| 2018/0369573 A1 | 12/2018 | Cholette et al. |
| 2019/0001139 A1 | 1/2019 | Mishra et al. |
| 2020/0046980 A1 | 2/2020 | Moffitt et al. |

OTHER PUBLICATIONS

Bartsch et al., Stimulation of the Greater Occipital Nerve Induces Increased Central Excitability of Dural Afferent Input, Guarantors of Brain, 2002, in 14 pages.
Carod-Artal et al., Tackling Chronic Migraine: Current Perspectives, Dove Press Journal: Journal of Pain Research, Apr. 8, 2014 in 10 pages.
Dodick et al., Safety and Efficacy of Peripheral Nerve Stimulation of the Occipital Nerves for the Management of Chronic Migraine: Long-term Results from a Randomized, Multicenter, Double-blinded, Controlled Study, Cephalalgia vol. 35(4), International Headache Society, 2015 in 15 pages.
Haub et al., 2013 World Population Data Sheet.
Headache Classification Committee of the International Headache Society, The InternationalClassification of Headache Disorders, 3rd edition, Cephalalgia vol. 33 (9), International Headache Society, 2013 in 180 pages.
Latinovic et al., Headache and Migraine in Primary Care: Consultation, Prescription and Referral Rates in a Large Population, J Neural Neurosurg Psychiatry, 2006 in 3 pages.
Magis et al., Central Modulation in Cluster Headache Patients Treated with Occipital Nerve Stimulation: An FDG-PET Study, BMC Neurology, 2011 in 9 pages.
Matharu, Botox Botulinum Toxin Type A, BoNTA, Allergan in the Management of Chronic Migraine, Allergan Ltd., 2010 in 2 pages.
Matharu et al., Central Neuromodulation in Chronic Migraine Patients with Suboccipital Stimulators: a PET Study, Advanced Access, Nov. 7, 2003 in 11 pages.
Matthews et al., The Response of a Single End Organ, Physiological Laboratory, Cambridge in 49 pages.
Menken et al., The Global Burden of Disease Study, Arch Neurol vol. 57, Mar. 2000 in 3 pages.
Migraine Facts, Migraine Research Foundation in 4 pages.
Miller et al., Neurostimulation in the Treatment of Primary Headaches, Pract Neurol, 2016, in 14 pages.
Novartis, Novartis Announces AMG 334 Significantly Reduces Patients' Monthly Migraine Days in Phase II Study of Chronic Migraine Prevention, Novartis Media Release.
Saper et al., Occipital Nerve Stimulation for the Treatment of Intractable Chronic Migraine Headache: ONSTIM feasibility Study, Cephalalgia 31(3), International Headache Society, 2010 in 15 pages.
Schramm et al., Epidemiological Profiles of Patients with Chronic Migraine and Chronic Tension-type Headache, The Journal of Headache and Pain 2013 in 8 pages.
Silberstein et al., Efficacy and Safety of Topiramate for the Treatment of Chronic Migraine: A Randomized, Double-Blind, Placebo-Controlled Trial, American Headache Society, 2007 in 11 pages.
Silberstein et al., Safety and Efficacy of Peripheral Nerve Stimulation of the Occipital Nerves for the Management of Chronic Migraine: Results from a Randomized, Multicenter, Double-blinded, Controlled Study, Cephalalgia 32(16), International Headache Society 2012 in 15 pages.
Vincent et al., Reduction of Calcitonin Gene-Related Peptide in Jugular Blood Following Electrical Stimulation of Rat Greater Occipital Nerve, Cephalalgia 1992 in 5 pages.

\* cited by examiner

| Specifications | |
|---|---|
| Part Number | D-0020 |
| Nominal Voltage | 3.65 Volts |
| Voltage Range | 3.0-4.1 Volts |
| Capacity | 50 mAh @ C/5 and 20°C |
| Maximum Recommended Charging Rate | C/2 |
| Cycle Life at 37°C | >80% Capacity After 1000 Cycles C/2 Charge to 4.1V C/2 Discharge to 3.0V |
| Dimensions | See Detail on Back |
| Volume | 0.88 cc |
| Weight | 2.5 g |
| Energy Density | 228 Wh/L |
| Operating Temperature | 37°C |
| Recommended Storage Conditions | 20±5°C |
| Case Material | Titanium |
| Terminals | Molybdenum |

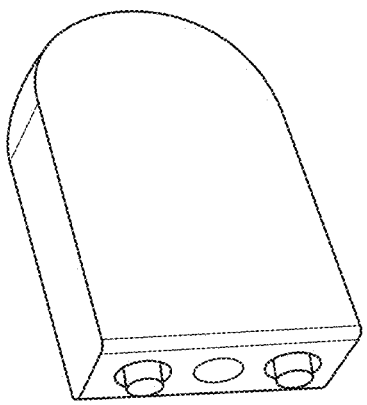

*FIG. 7*

Time

Modulation Waveform 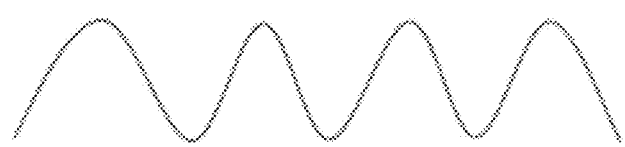
Constant Stimulation Waveform 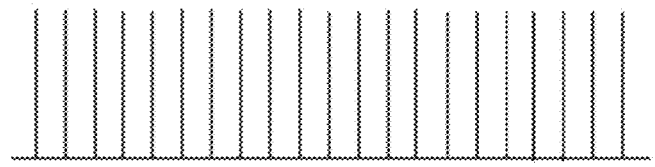
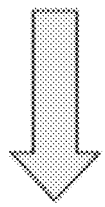
Superimposed Waveforms 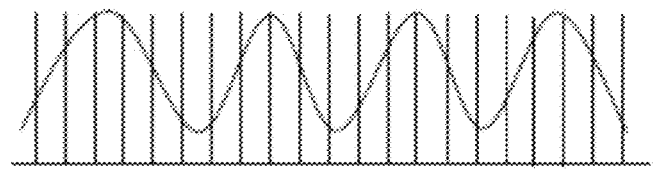
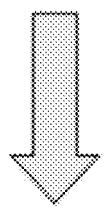
Resulting Stimulation Waveform 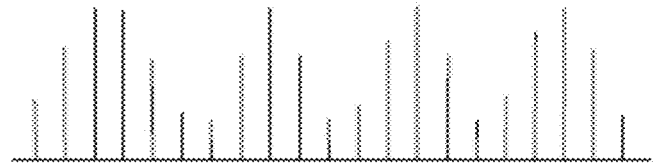
Figure 17a – Regular Phase Amplitude Clipping Stimulation Modulation Waveform
Constant Stimulation Waveform
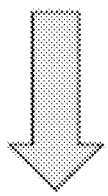
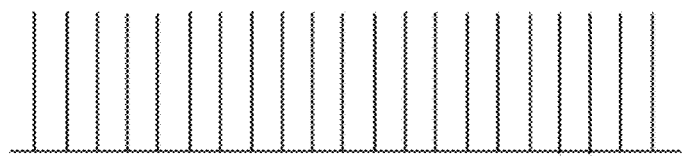
Superimposed Waveforms
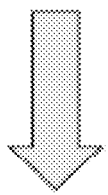
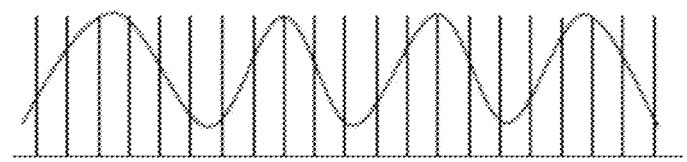
Resulting Stimulation Waveform
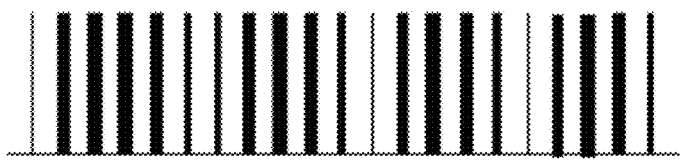
*FIG. 17B*

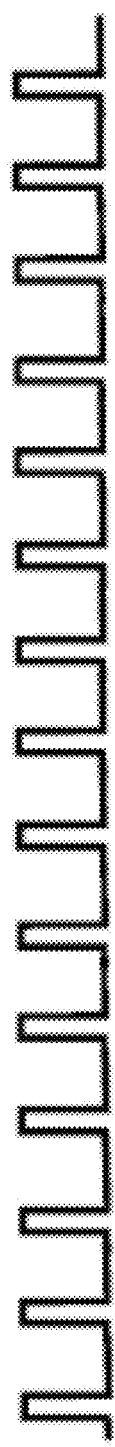
FIG. 20
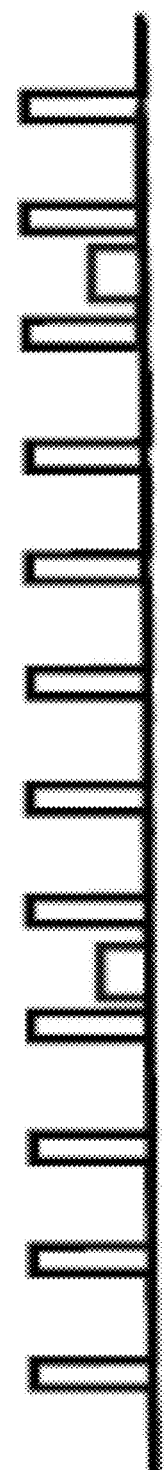
FIG. 21

SYSTEM AND METHODS FOR THERAPEUTIC STIMULATION

CROSS-REFERENCE TO RELATED APPLICATIONS

The present application is a continuation of U.S. patent application Ser. No. 15/961,751, filed Apr. 24, 2018, now U.S. Pat. No. 11,779,755, which claims priority benefit to U.S. Provisional Application No. 62/489,925, filed Apr. 25, 2017, entitled "SYSTEM AND METHODS FOR THERAPEUTIC STIMULATION," which is hereby incorporated herein by reference in its entirety. Any and all applications for which a foreign or domestic priority claim is identified in the Application Data Sheet as filed with the present application are hereby incorporated by reference under 37 CFR 1.57 and made a part of this specification. Any and all publications or patent applications mentioned herein are hereby incorporated by reference to the same extent as if each individual publication or patent application was specifically and individually indicated to be incorporated by reference.

BACKGROUND

Field of the Invention

The present disclosure relates to systems and methods of electrical stimulation, which can be utilized to treat medical conditions and/or disorders.

Description of the Related Art

Many people around the world are afflicted by chronic neurological disorders including, but not limited to, Chronic Pain, Parkinson's, Essential Tremor, Urinary Incontinence, Heart Failure & Epilepsy. Electrical stimulation of the nervous system is widely used to treat these chronic conditions. However, these therapies have numerous opportunities for improvement. For example, a large number of people in the United States are afflicted with Chronic Migraine ("CM"), a highly debilitating neurological disorder. While abortive and preventative medicines exist, a significant part of the CM population are termed intractable and do not respond adequately to these treatments. It is estimated that over 318 thousand Americans suffer from Intractable Chronic Migraine ("ICM"). These patients are highly disabled by their disease and are faced with a significantly lowered productivity and quality of life with few options for relief. These patients who are unresponsive to preventative medicine may progress to more invasive and problematic therapies such as opioid injections, nerve blocks and surgery. Techniques such as Occipital Nerve Stimulation ("ONS") are promising therapies for a variety of headache disorders such as CM and ICM.

SUMMARY

A system for providing electrical stimulation to biological tissue to treat one or more medical conditions. The system can include one or more leads configured to be positioned in contact with or proximate to biological tissue that is proximate one or more occipital or peripheral nerves. The one or more leads can include one or more electrodes. The system can further include an implantable pulse generator configured to deliver electrical stimulation to the biological tissue via the one or more leads. In some cases, the implantable pulse generator can have a size of less than 5 cc and/or can be implanted directly in an occipital region of a patient or proximate the occipital region. The system can further include a power source configured to operatively connect and supply power to the implantable pulse generator. The system can further include one or more processors configured to communicate with the implantable pulse generator. The one or more processors can operate the implantable pulse generator to cause the implantable pulse generator to deliver the electrical stimulation to the biological tissue via the one or more leads. The implantable pulse generator can deliver the electrical stimulation by applying a stimulation waveform or a stimulation pattern. The stimulation waveform can include a series of stimulation pulses that can vary over time, which can reduce an effect of neural accommodation or adaptation.

The system of the preceding paragraph may also include any combination of the following features described in this paragraph, among others described herein. At least one of an inter-pulse frequency, a pulse amplitude, or a pulse width of the series of stimulation pulses can increase over the time. For example, the at least one of the inter-pulse frequency, the pulse amplitude, or the pulse width of the series of stimulation pulses can increase linearly or exponentially over the time. In addition or alternatively the at least one of an inter-pulse frequency, a pulse amplitude, or a pulse width of the series of stimulation pulses can decrease over the time. For example, the at least one of the inter-pulse frequency, the pulse amplitude, or the pulse width of the series of stimulation pulses can decrease linearly or exponentially over the time.

The system of any of the preceding paragraphs may also include any combination of the following features described in this paragraph, among others described herein. At least one of an inter-pulse frequency, a pulse amplitude, or a pulse width of the series of stimulation pulses can increase over the time and/or a different one of the at least one at least one of the inter-pulse frequency, the pulse amplitude, or the pulse width of the series of stimulation pulses can decrease over the time. The time can include a first time period and a second time period. The series of stimulation pulses can be a first series of stimulation pulses over the first time period, and the stimulation waveform can include a second series of stimulation pulses over the second time period. A pattern of the second series of stimulation pulses can match a pattern of the first series of stimulation pulses. For example, the second series of pulses can be a copy of the first series of pulses. The pattern of the second series of stimulation pulses can alternatively include an inverted pattern of a pattern of the first series of stimulation pulses. In some cases, the stimulation waveform can include more than two series of pulses. The stimulation waveform can include one or more relaxation pauses between at least some of the plurality of pulses. The one or more processor can be further configured to adjust the stimulation waveform based at least in part on at least one of user input, a time of day, a user activity level, a physiological parameter, or a predetermined pattern.

A method for providing electrical stimulation to biological tissue to treat one or more medical conditions. The method can include selecting, using one or more processors, a stimulation waveform of a plurality of stimulation waveforms that reduce an effect of neural adaption. Each of the plurality of stimulation waveforms can include a series of stimulation pulses. The method can further include operating, using the one or more processors, an implantable pulse generator to deliver electrical stimulation to biological tissue that is proximate one or more occipital or peripheral nerves.

To deliver the electrical stimulation, the one or more processors can cause the implantable pulse generator to apply the selected stimulation waveform via one or more leads positioned in contact with or proximate to the biological tissue. The one or more leads can include one or more electrodes.

The method of the preceding paragraph may also include any combination of the following features or steps described in this paragraph, among others described herein. At least one of an inter-pulse frequency, a pulse amplitude, or a pulse width of the series of stimulation pulses of the selected stimulation waveform can increase or decrease over the time. At least one of an inter-pulse frequency, a pulse amplitude, or a pulse width of the series of stimulation pulses of the selected stimulation waveform can increase over the time, while a different one of the inter-pulse frequency, the pulse amplitude, or the pulse width of the series of stimulation pulses of the selected stimulation waveform can decrease over the time.

The method of any of the preceding two paragraphs may also include any combination of the following features or steps described in this paragraph, among others described herein. The time can include a first time period and a second time period. The series of stimulation pulses can be a first series of stimulation pulses over the first time period. The selected stimulation waveform can include a second series of stimulation pulses over the second time period. A pattern corresponding to the first second series of stimulation pulses can match a pattern corresponding to the second series of stimulation pulses The selected stimulation waveform can include one or more relaxation pauses between at least some of the plurality of pulses. The selection is based at least in part on at least one of a user input, a time of day, a user activity level, a physiological parameter, or a predetermined pattern.

For purposes of summarizing the disclosure, certain aspects, advantages and novel features are discussed herein. It is to be understood that not necessarily all such aspects, advantages or features will be embodied in any particular embodiment of the invention and an artisan would recognize from the disclosure herein a myriad of combinations of such aspects, advantages or features.

BRIEF DESCRIPTION OF THE DRAWINGS

Embodiments of the present disclosure will now be described hereinafter, by way of example only, with reference to the accompanying drawings in which:

FIG. 7 illustrates an example battery of an ONS micro pulse generator.

FIG. 17A illustrates an example of Regular Phase Amplitude Clipping Stimulation.

FIG. 17B illustrates an example of Regular Phase Width Modulated Stimulation.

FIG. 20 illustrates example waveforms for multicomponent therapeutic stimulation.

FIG. 21 illustrates example hybrid waveforms.

DETAILED DESCRIPTION

The human nervous system is vastly complex in its behavior. It is characterized by the electrical firing of neurons in highly organized afferent and efferent circuits which control thought, behavior and homeostasis. Pathological medical conditions arise when this electrical activity becomes abnormal. Numerous therapies exist for these medical conditions including neurostimulation therapies which utilize electrical impulses to stimulate the nervous system in the hope of controlling or affecting the underlying medical condition. Classically, this electrical stimulation has used static, or very simple electrical patterns. Improvements in the systems, methods and techniques for the application of therapeutic stimulation or modification of a patient are needed for greater effectiveness, patient comfort and therapy durability.

Electrical stimulation of the nervous system is widely used to treat numerous diseases such as but not limited to: Chronic Pain, Parkinson's, Essential Tremor, Urinary Incontinence, Heart Failure & Epilepsy. It is also well recognized that the nervous system can become progressively desensitized to the stimulation and that beneficial therapeutic effects may lessen or disappear. This desensitization is thought to be the result of the physiological phenomenon of neural adaptation.

Neural adaptation is a change over time in the responsiveness of the nervous system to a constant stimulus. It is usually experienced as a change in the perceived stimulus.

Figure 3:
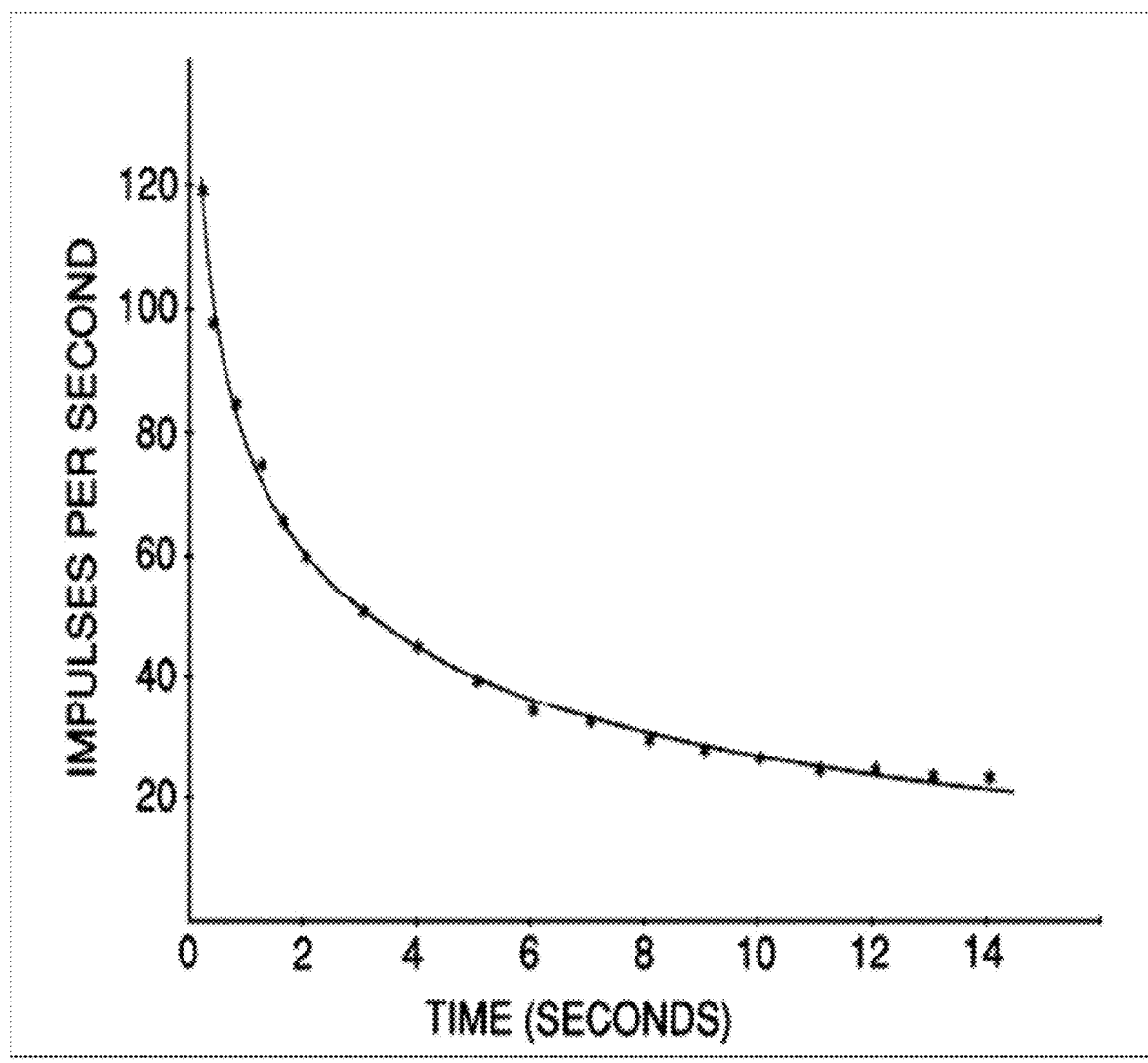
FIG. 3 illustrates a graph of firing frequency of a sensory nerve demonstrating adaptation.

For example, if one rests one's hand on a table, one immediately feels the table's surface on one's skin. Within a few seconds, however, one ceases to feel the table's surface. The sensory neurons stimulated by the table's surface respond immediately, but then respond less and less until they may not respond at all; this is an example of neural adaptation. A classic physiology experiment recorded the firing frequency of a sensory nerve while a limb is under constant load. As the load is applied, the initial firing rate of the sensory nerve is quite high and exceeds 120 Hz, however as time progresses the firing rate quickly decays to approximately 25 Hz after 14 seconds (FIG. 3). This rapid decay in firing frequency of a peripheral sensory nerve under constant sensory input is classic neural adaptation.

Figure 4:
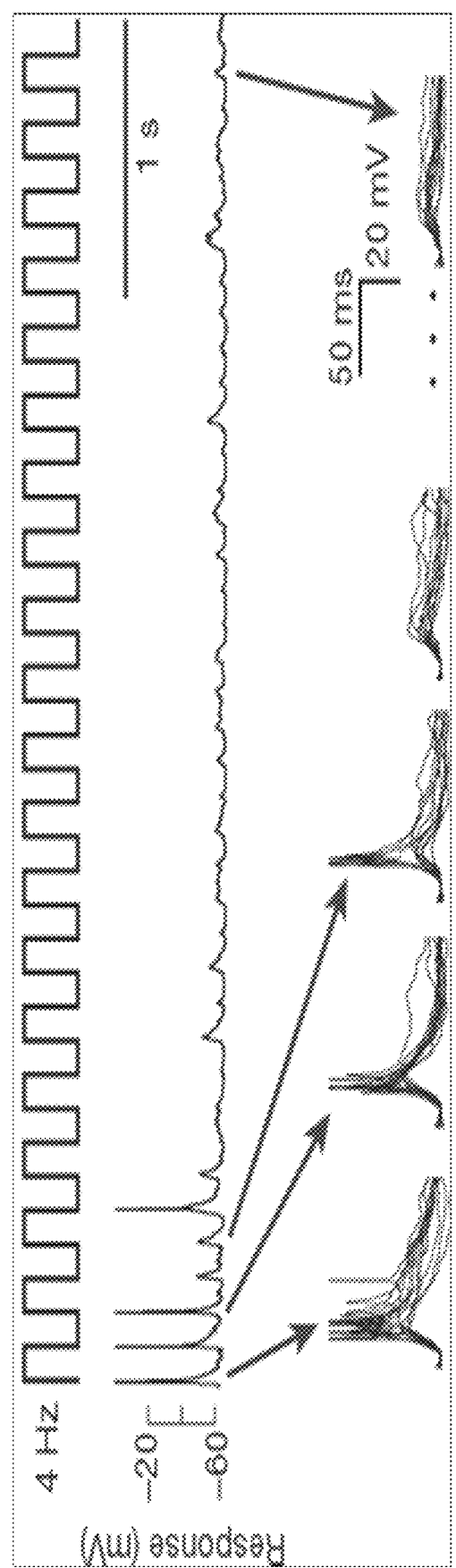
FIG. 4 illustrates a graph of sensory adaptation of the cortex in response to a constant 4 Hz stimulation of the rat whisker[20].

Neural adaptation is also thought to happen at a more central level such as the cortex. Synaptic depression of thalamocortical synapses underlies sensory adaptation in the cortex. FIG. 4 illustrates the sensory adaptation of the cortex in response to a constant 4 Hz stimulation of a rat whisker. The primary whisker of a rat is stimulated at 4 Hz (top of FIG. 4) and the response of a cortical neuron in the corresponding region of barrel cortex is measured with an intracellular recording electrode (middle of FIG. 4). Even though whisker stimulation is maintained, action potentials are only evoked in the cortical cell during the first second of stimulation. This stimulation is repeated 12 times. An expanded view of the responses observed in the cortical cell during different periods of stimulation (bottom) shows that as the train progresses. EPSPs became progressively smaller and eventually are no longer able to evoke action potentials. Extensive experiments suggest that synaptic depression at the thalamocortical synapse underlies the sensory adaptation observed during whisker stimulation.

Sensory adaptation is believed to underlie and limit the efficacy of all therapeutic neurostimulation. Techniques aimed at overcoming adaptation will serve to increase therapy efficacy and durability. There has been much attention in the area of more efficacious stimulation for the treatment of these neurological disorders. The current state-of-the-art is to stimulate nervous tissue in a constant manner. This disclosure discusses introducing variability to the electrical stimulation in order to overcome this natural neural adaptation. There has been previous art that discloses random or non-deterministic stimulation in attempt to overcome this natural phenomenon. This disclosure discloses variable but deterministic variability. The potential advantage of deterministic stimulation is the neuromodulation efficacy will be both repeatable and a reproducible in addition to presenting the neural tissue with variation to overcome natural neural accommodation.

Figure 1:
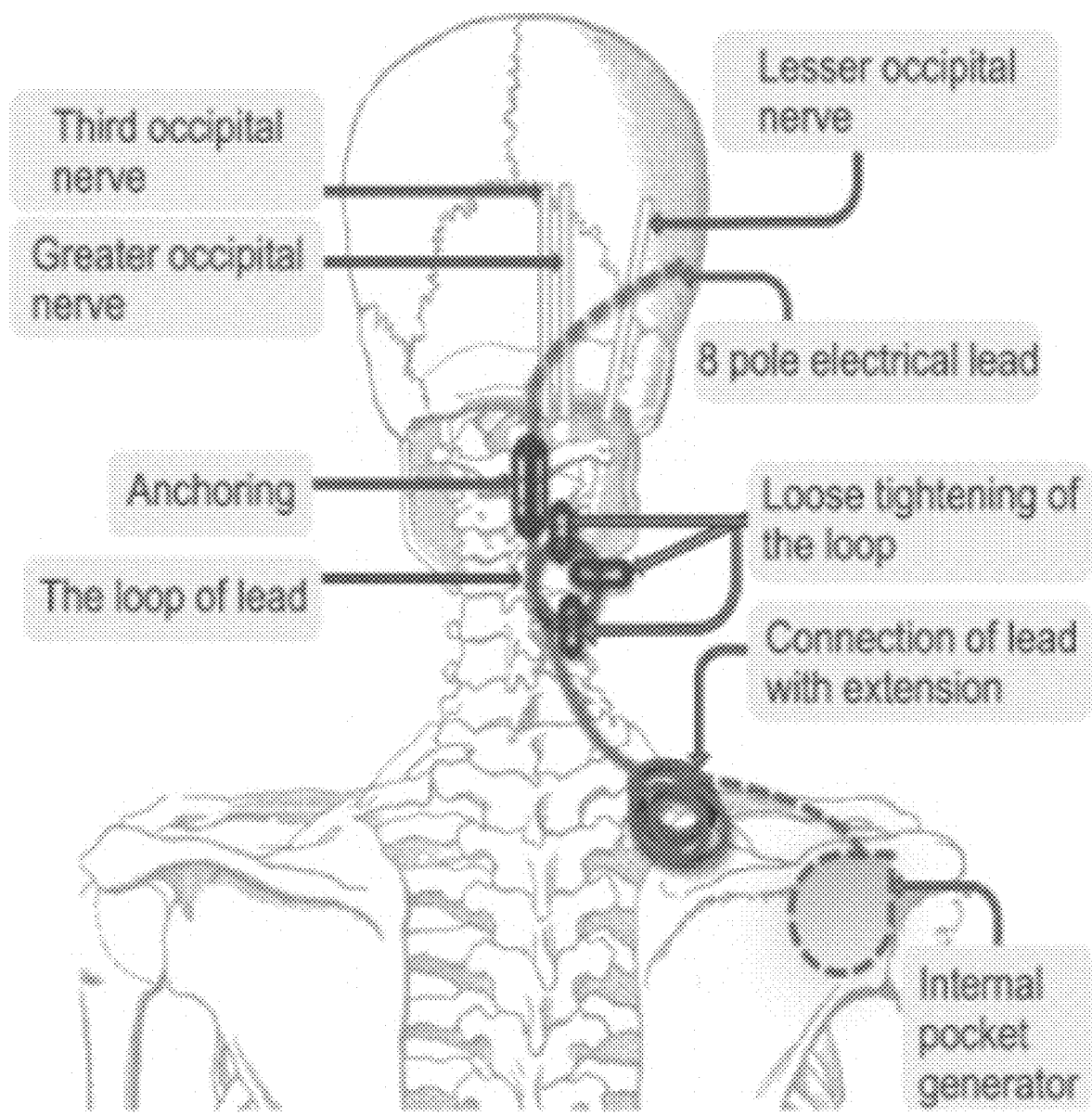
FIG. 1 illustrates an example spinal cord stimulator where the implantable pulse generator is placed below the neck and the leads are tunneled to the occipital region.

From a hardware perspective, there are no implantable devices/systems specifically designed for Peripheral Nerve Stimulation ("PNS") or Occipital Nerve Stimulation ("ONS"). As mentioned before, this disclosure will focus on ONS for a matter of illustration. It is common practice to implant spinal cord stimulation ("SCS") systems in the occipital region for the treatment of Chronic Migraine ("CM") & Intractable Chronic Migraine ("ICM"). The SCS devices are not approved by the FDA for the treatment of migraines; while common, these implants are performed off-label by the treating physician. For instance, FIG. 1 illustrates a traditional spinal cord stimulator where the implantable pulse generator is placed below the neck and the leads are tunneled to the occipital region. This is the typical off-label use of a spinal cord stimulator that is labeled for chronic pain of the trunk and/or limbs to treat various headache disorders.

Studies indicate that ONS is effective at reducing the number of headache days per month and improves other important metrics such as disability and quality of life. ONS for the treatment of CM & ICM has been studied in multiple clinical trials, including three randomized clinical trials summarized in Table 1 that show a 3.1 to 18.2 reduction in headache days per month.

TABLE 1

Example Randomized Clinical Trials Reporting on ONS for CM & ICM.

| Publication | Study Design | Follow-Up | Results |
|---|---|---|---|
| Saper et al., 2010, (ONSTIM Study) | Multicenter, parallel group, N = 67. | 3 months. | Reduction of 8.1 headache days per month in the ONS ancillary group vs the medically managed group. |
| Serra & Marchioretto, 2012. | Single center, crossover, N = 30. | 1 month for controlled phase. 12 months after open label. | Reduction of 18.2 headache days per month in the ONS ON group vs. the medically managed group. |
| Silberstein et al., 2012, (RELIEF Study). | Multicenter, parallel group with 2:1 randomization, N = 157. | 3 months. | Reduction of 3.1 headache days per month in the ONS group vs the sham group. |

The reported efficacy of ONS as a therapy of CM & ICM is superior to that of current "gold standard" preventative treatments, such as Botox and Topiramate. ONS also compares favorably to the recent class of drugs being developed by the pharmaceutical industry called CGRP antagonists, as well as recent external vagus nerve stimulators as illustrated in Table 2. This table represents the net reduction of headache days per month after the comparable placebo or sham treatment has been subtracted.

TABLE 2

Comparative Efficacy of ONS for CM & ICM.

| Therapy Type | Headache Days per Month Reduction vs Placebo/Sham |
|---|---|
| Botox | 1.8 |
| Topiramate | 1.7 |
| CGRP Antagonist | 2.4 |
| nVNS | 1.3 |
| ONS | 3.8 |

Figure 2:
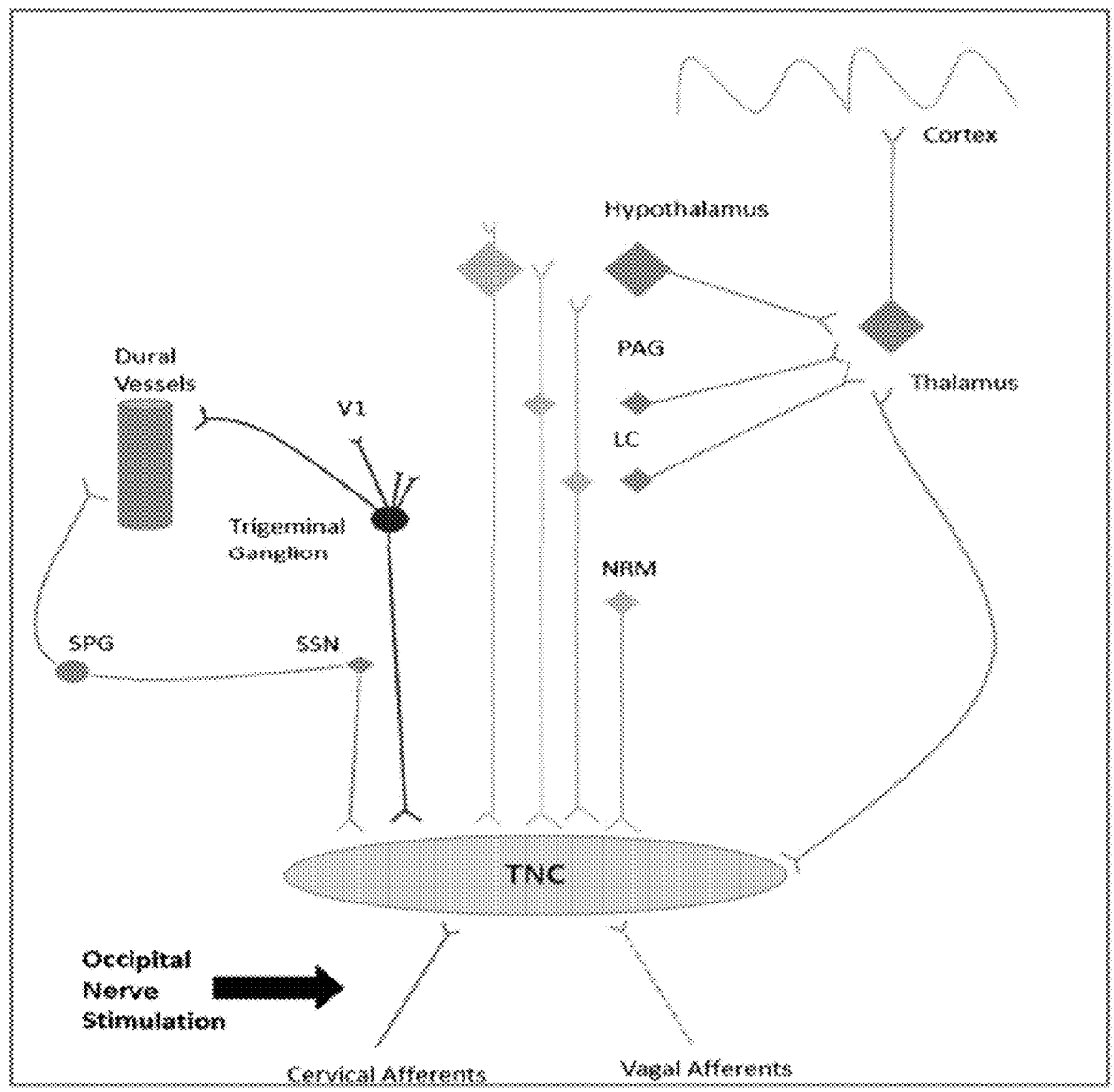
FIG. 2 illustrates putative mechanisms of action of Occipital Nerve Stimulation ("ONS") for Chronic Migraine ("CM") & Intractable Chronic Migraine ("ICM").

The efficacy of ONS for CM & ICM is well documented in the literature. While the exact mechanism(s) of action remain unclear, there is published evidence that ONS affects the Trigeminal Nucleus Complex, Anterior Cingulate Cortex, Basal Ganglia, Pons, Thalamus, Periaqueductal Grey, Cortex, Locus Coeruleus, Hypothalamus and Dural Vessel Innervation. Stimulation of the Occipital Nerves modulates the Trigeminal Nucleus Complex ("TNC") by way of afferent fibers that enter the spinal cord via the dorsal ramus of C2. Projections from the TNC to the Thalamus further modulate cortical circuits as well as the Hypothalamus, Periaqueductal Grey and Locus Coeruleus which further modulate the activity of the TNC via putative descending inhibition. In parallel, ONS modulates afferent activity to the dural vessels via the Sphenopalatine Ganglion which reduces the release of CGRP and consequent pain processing via the V1 branch of the Trigeminal Nerve as illustrated in FIG. 2.

Despite its positive clinical efficacy, ONS is accompanied by an unacceptable level of device related adverse events. Most of these adverse events are due to utilizing a neuromodulation system such as spinal cord stimulation ("SCS") systems which were not designed for the occipital region. The major adverse events reported in the three studies are summarized in Table 3 and are mainly attributable to hardware deficiencies. For example, the leads from the implantable pulse generator (IPG) to the stimulation site must traverse the neck, a highly mobile joint, putting undue mechanical stress on the lead, causing a high incidence rate of lead migration. The excessive tunneling required to deploy the lead from the IPG to the stimulation site contributed significantly to the persistent pain/discomfort and the infection rates. The lack of efficacy in certain patients is also likely attributable to the lead migration which creates ineffective stimulation of the nerve. Lastly wound site complications, skin erosion and lead breakage are also attributable to hardware deficiencies for this application.

to implant the pulse generator near the submastoid process on either side and the place the leads subcutaneous transversely across the occipital nerve network.

Leads. There are various types of stimulation wires, or leads, which can be used to stimulate the target tissue structures. Typical leads used for Spinal Cord Stimulation are percutaneous or paddle leads. Percutaneous leads are tubular in shape and have circumferential electrodes that stimulate omni-directionally. Paddle leads are flat in shape and have flat or surface electrodes that can stimulate uni-directionally or bi-directionally. Traditionally, percutaneous leads have been used for ONS due to case of placement. In addition, by using circumferential electrodes the stimulation energy would also stimulate the tactile fibers of the occipital nerves potentially increasing the probability of recruiting nervous tissue. One of the benefits of the paddle electrodes is that they are slim and have a lower profile than the percutaneous leads. In addition, because the paddle leads stimulate in one direction, this type of lead may also be more

TABLE 3

Adverse Events Reported from Randomized Clinical Trials on ONS for CM & ICM.

| Adverse Event | Saper et al. (n = 51) | Serra & Marchioretto (n = 30) | Silberstein et al. (n = 157) | Rate |
|---|---|---|---|---|
| Lead migration | 12 | 3 | 20 | 14.71% |
| Persistent pain/discomfort at implant side | | | 23 | 9.66% |
| Infection | 11 | 2 | 7 | 8.40% |
| Lack of efficacy/benefit | 8 | | 6 | 5.88% |
| Expected post-operative pain, numbness at IPG or lead site | 1 | | 9 | 4.20% |
| Incision/wound site complications | 4 | | 4 | 3.36% |
| Undesirable changes in stimulation | | | 7 | 2.94% |
| Skin erosion | | | 6 | 2.52% |
| Allergic reaction to surgical materials | | | 4 | 1.68% |
| Lead breakage/fracture | 1 | | 2 | 1.26% |
| Disconnection of device | | | 3 | 1.26% |
| Nausea/vomiting | 1 | | 1 | 0.84% |
| Incision site pain | 2 | | | 0.84% |
| Neck pain | 2 | | | 0.84% |
| Unintended changes in headache, (severity, type or frequency) | | | 1 | 0.42% |
| Other | 14 | | 4 | 7.56% |
| TOTAL | 56 | 5 | 97 | 66.39% |

Figure 5:
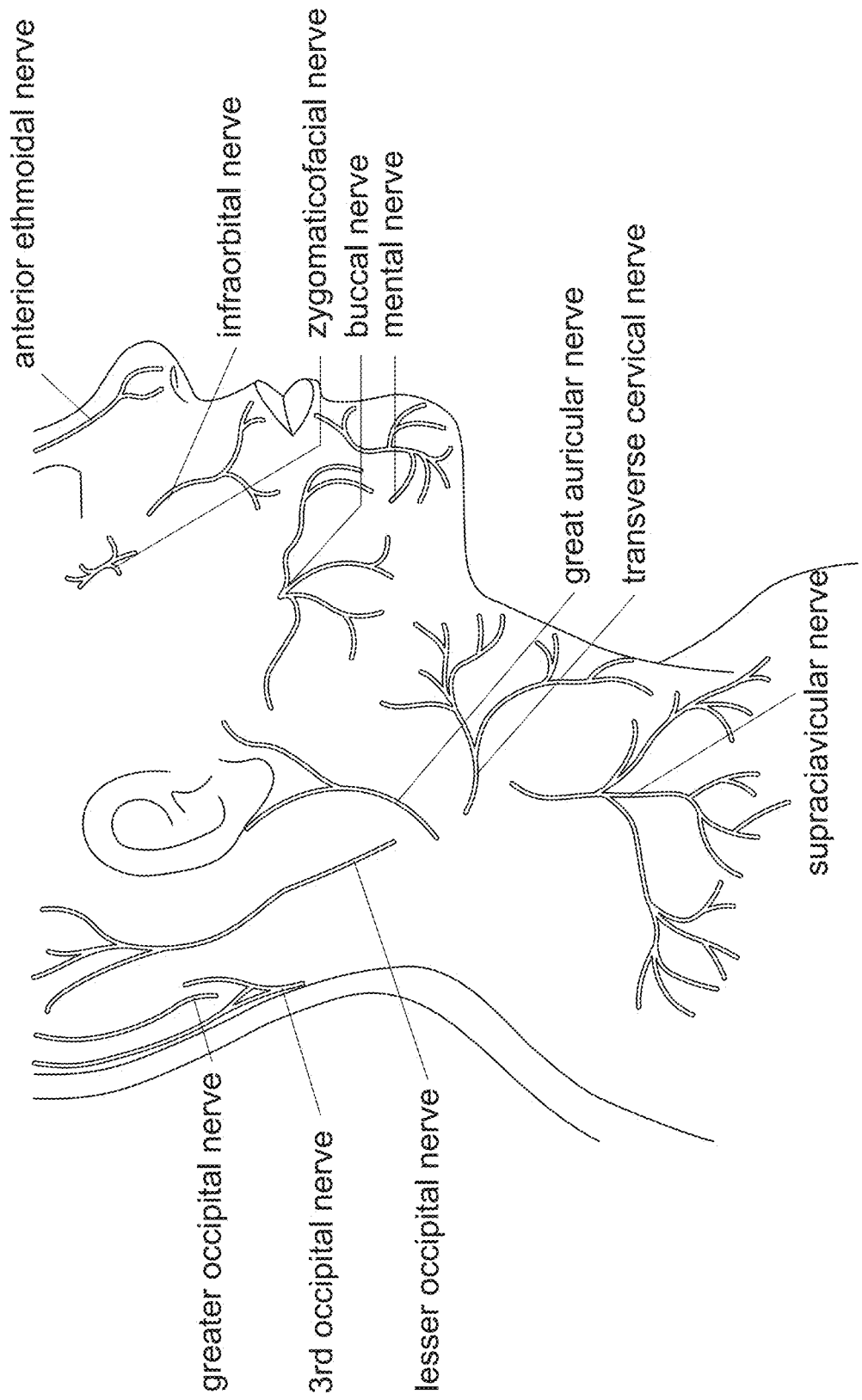
FIG. 5 illustrates anatomy of the occipital and auricular nerves.

Implant Location. The tissue targeted by the electrical stimulation of ONS for CM & ICM is generally the Greater Occipital Nerve ("GON"), however there are likely therapeutic benefits to also stimulating the Lesser Occipital Nerve ("LON"), Third Occipital Nerve ("TON") and importantly the Great Auricular Nerve ("GAN"). FIG. 5 illustrates the anatomy of the GON, LON, TON, GAN. Each nerve has a left and right counterpart and both must be stimulated to achieve maximum therapeutic efficacy.

Figure 6A:
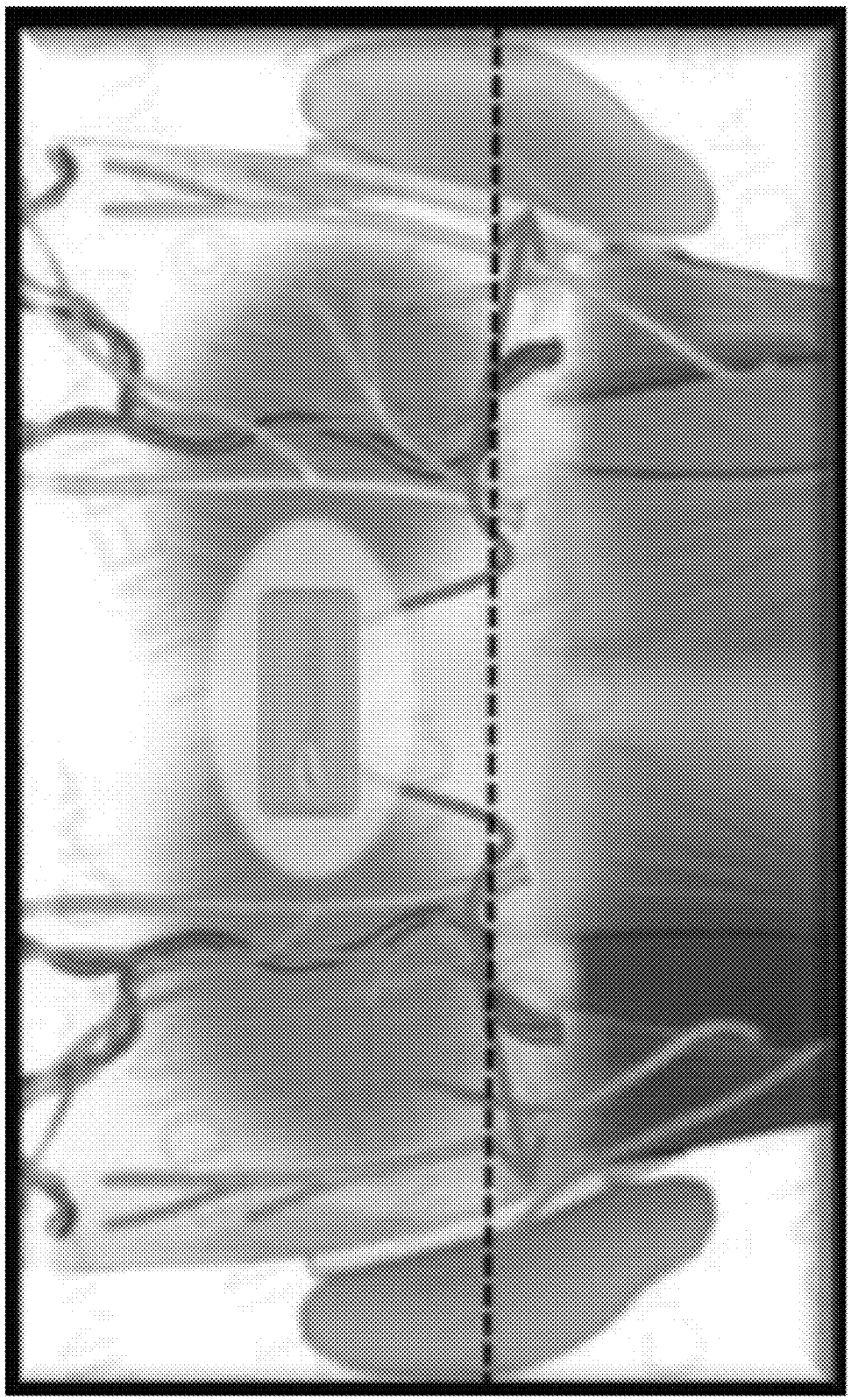
FIG. 6A illustrates an example diagram of a micro pulse generator and leads implanted in the occipital region.

In one embodiment, to deliver therapy to the occipital and auricular nerves without requiring a wire/lead to traverse the neck as illustrated in (FIG. 1), a micro pulse generator having a size of less than 5 cc is implanted directly in the occipital region (FIG. 6A). From this micro pulse generator, leads or wires deliver the electrical stimulation energy to the left and right target nerves. Another potential embodiment is to implant the pulse generator just below the occiput and place the leads to the lower part of the ear. By implanting in this manner, the leads and associated electrodes would be placed over or in proximity to the target occipital nerves. Another embodiment would be to run the leads/wires along the occipital ridge. Another potential embodiment would be energy efficient in recruitment of the main nerve trunks such as the GON or other family of nerves. Independent of lead type selected, it may also be beneficial to have an anchoring mechanism on the distal end of the lead such as polymer tines or suture holes to fasten the end of the lead to the tissue facia.

Figure 6B:
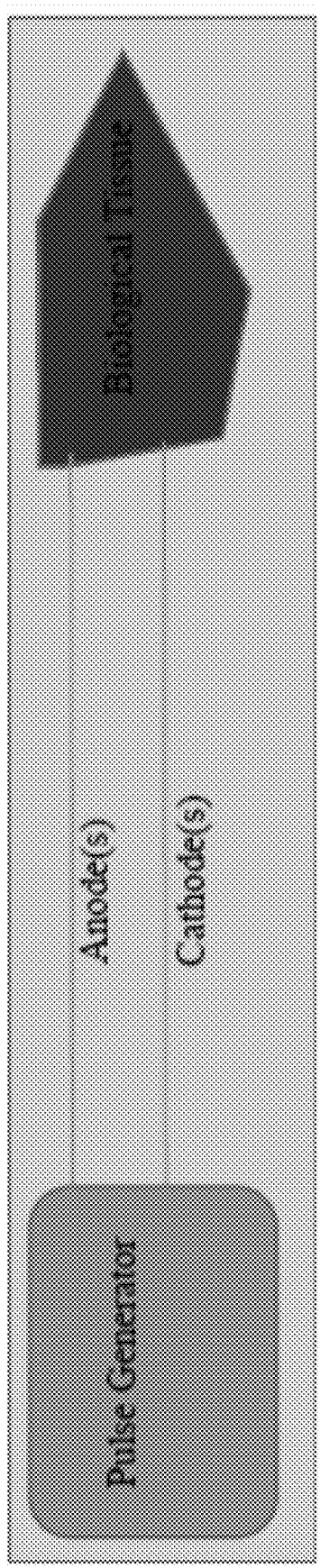
FIG. 6B illustrates a diagram of an example Neuromodulation system.

Pulse Generator. This disclosure discloses a method of determining how the parameters that control the stimulation of biological tissue evolve. This methodology can be implemented in any pulse generator. The construction of the pulse generator is not part of this disclosure but can be well understood and can be implemented by one skilled in the art. In exemplary fashion, we illustrate the components of a standard neuromodulation system. The neuromodulation system comprises a pulse generator and leads which connect the pulse generator to the biological tissue (FIG. 6B).

Typically, a pulse generator is powered by a battery, but may be also powered by other means. Typically, the pulse generator is connected to the biological tissue by one or more wires called leads. There is at least one anode and one cathode for stimulation, but more may be present. In addition, electrodes located on the pulse generator itself may be used for stimulation, for example the metallic enclosure, or can of the device, can be used as an anode.

Typically, a pulse generator comprises several components, such as those listed below. The construction of a micro pulse generator small enough to fit in the occipital region will require one skilled in the art to make design choices that minimize the device footprint while allowing sufficient energy to provide therapeutic electrical stimulation at a reasonable recharge interval of approximately 7 days. The following sections highlight some of the major building blocks of such a micro pulse generator. This serves the purpose of teaching one skilled in the art how to build such a stimulator but should not be considered limiting in any sense.

Battery (Primary Cell or Rechargeable). In order to meet the size and power constraints of the ONS micro pulse generator, a rechargeable battery of approximately 50 mAHr will be used. An example of such a rechargeable battery is the Contego 50 mAHr battery from Eagle Picher illustrated and specified in FIG. 7.

Figure 8A:
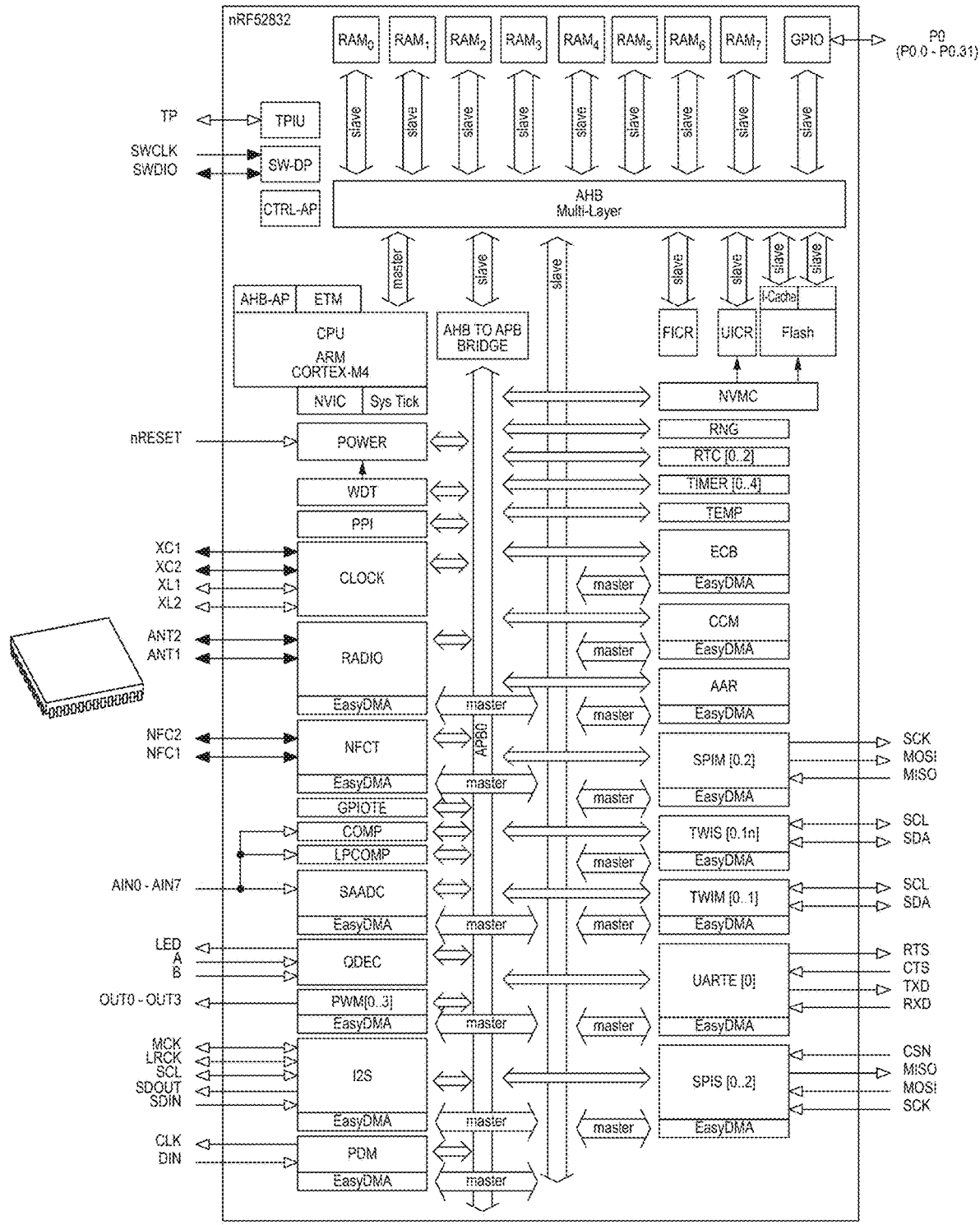
FIG. 8A illustrates an example processor of an ONS micro pulse generator.

Microcontroller/CPU. The micro pulse generator requires a CPU to control its operations and implement the stimulation logic and other product features. There are numerous options available on the market, however the recent "System on a chip" ("SoC") has the distinct advantage of integrating multiple components on a single chip. The primary determinants of selecting such a chip are its specific capabilities, size and power consumption profile. The Nordic nRF52 family (shown in FIG. 8A) is one example of a suitable chip for the ONS application.

The nRF52 family of SoC chips has features that facilitate the development of a small volume micro pulse generator, such as:
  ARM-M4 Cortex Microprocessor and FPU.
  Flash memory and RAM.
  Low power consumption sleep mode.
  12 bit ADC.
  32 bit counters/timers to implement stimulation and control algorithms.
  32 GPIO ports to enable external peripheral control.
  SPI/I2C connectivity with DMA to connect the nRF52 to external peripherals.
  Bluetooth Low Energy Rx/Tx transceiver to communication with an off the shelf external unit.
  HW data encryption to enable secure data transmission.
  NFC-A tag that allows device wakeup without BLE involvement to save power.

Recharging Circuit. Typically custom designed to transfer energy via inductive coupling. Circuit is designed to recharge the battery quickly while limiting the temperature excursions of the micro pulse generator.

Antenna/Recharge Coil. Enable communication or charging of the battery with the external instrument via a predetermined protocol. This antenna may be located inside the pulse generator, in the header where the leads are connected, around the perimeter of the can or on the surface of the can. One embodiment of the pulse generator is to have the communication antenna and recharge coil as separate components. In another embodiment, the antenna and recharge coil can be tuned to serve both communication and recharging function.

Telemetry/Communications Unit (Inductive, MICS, Bluetooth-standard, Bluetooth Low Energy (BLE), ZigBee, Wifi 802.11a/b/g/n). Enables communication to the external instrument, may be on-board the SoC as in the case of the Nordic nRF52 family.

Energy Saving External Wakeup. The communication between the micro pulse generator and an external instrument such as an Android and/or Apple tablet can occur via the Telemetry/Communications unit which can utilize a communication protocol such as Bluetooth Low Energy (BLE). The circuitry responsible for the communications typically consumes a large amount of battery energy; it is therefore desirable to save energy by powering down the communications circuitry while not in use. However, once the communications circuitry has been disabled, a mechanism is required to re-enable it when the external instrument/ user initiates a communication session with the micro pulse generator. While it is possible for the micro pulse generator to periodically enable the communications circuitry to "poll" an external instrument, this scheme wastes energy as there is very little communications between the external instrument and the micro pulse generator. In fact, useless polling may waste more energy than that which is used to communicate over time. An attractive functionality is for the external instrument to have a means of enabling the communications circuitry in the micro pulse generator remotely. This can be achieved remotely by application of a magnet, or other means (such as near field communications) of triggering a "wake-up communications" interrupt in the micro pulse generator.

Figure 8B:
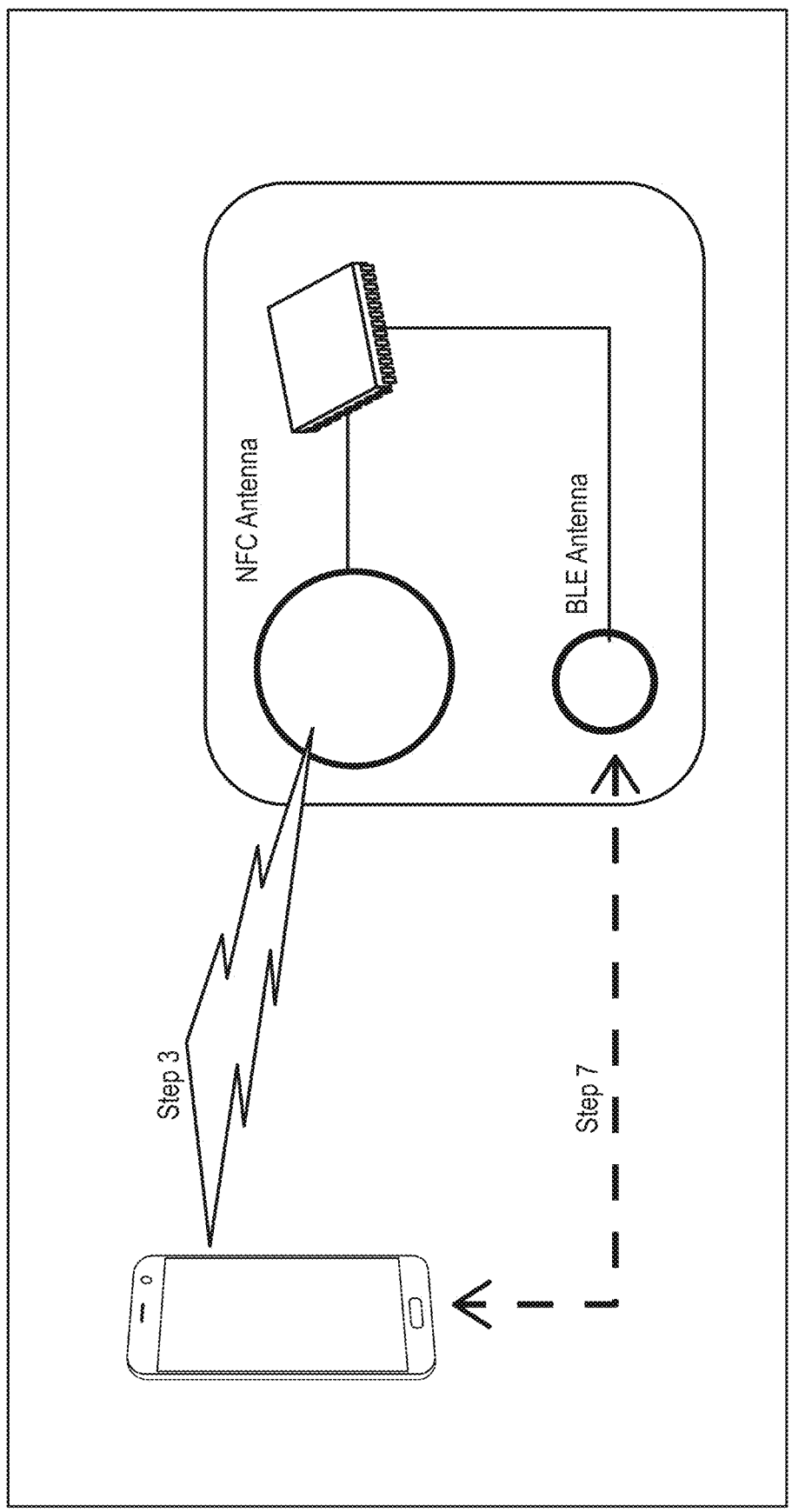
FIG. 8B illustrates example communications between a micro pulse generator and a mobile device.

The following example illustrates the use of a Near Field Communications (NFC) protocol adapted for Android and Apple devices to activate and enable the Bluetooth Low Energy (BLE) radio found in the Nordic nRF52832 SoC. See also, for example, FIG. 8B.
  1. User wishes to control the micro pulse generator.
  2. User places Android or Apple device near the micro pulse generator.
  3. Android or Apple device initiates NFC communication to micro pulse generator.
  4. NFC signal is received by the NFC antenna in the micro pulse generator. (User may now move the Android/Apple device away from the micro pulse generator.)
  5. Firmware on Nordic nRF52832 SoC is alerted of NFC communication by an interrupt (Wake-Up Communications).
  6. Firmware on the Nordic nRF52832 SoC activates the BLE radio and functionality.
  7. Communications occur between the Android/Apple device and the micro pulse generator via BLE.
  8. Once the communications session is ended by either party or a timeout occurs, the firmware on the nRF52832 SoC shuts down the BLE radio and functionality.
  9. Firmware on the nRF52832 SoC resets the NFC system in order to wait for the next wakeup from the Android/Apple device.

It is important to note that this is an example only. This power saving feature can be implemented using a variety of protocols and hardware configurations.

Output/Stimulation Unit (Charge Pump, DC-DC Converter, Switches, DC Blocking Caps). Circuitry under the control of the microprocessor and responsible for issuing stimulation pulses to the appropriate anode-cathode pair of stimulating electrodes. May also implement some functionality such as impedance measurements, voltage over-head detection, charge balancing and fault detection. The stimulation function could be in the configuration of an outboard circuit located on the PCB or integrated into a microprocessor chip.

Sensing Unit (Filters, Amplifier, ADC). Responsible for the measurement of external signals, specifically physiological electrical potentials.

The neuromodulation system hardware and software described in this disclosure can be similar in design, construction and operation to the following devices:

Cardiac stimulators such as pacemakers, ICD and CRT devices.

Implantable neurostimulation devices such as SCS, DBS, DRG and PNS devices.

External neurostimulation devices such as TENS units and trial therapy devices.

All of these above mentioned devices are connected to the biological tissue with wires called leads which may be used for stimulation (anodes & cathodes) or recording/sensing of biological activity. Furthermore, the stimulator, or pulse generator may be controlled externally by means of another device called a "programmer" which wirelessly communicates with the stimulation device and is able to control is behavior.

Form Factor. The form factor for the occipital implant location is critical for comfort and durability of the implant life. Several preferred embodiments are listed below which may be employed to provide a better fit for the micro pulse generator.

Figure 9:
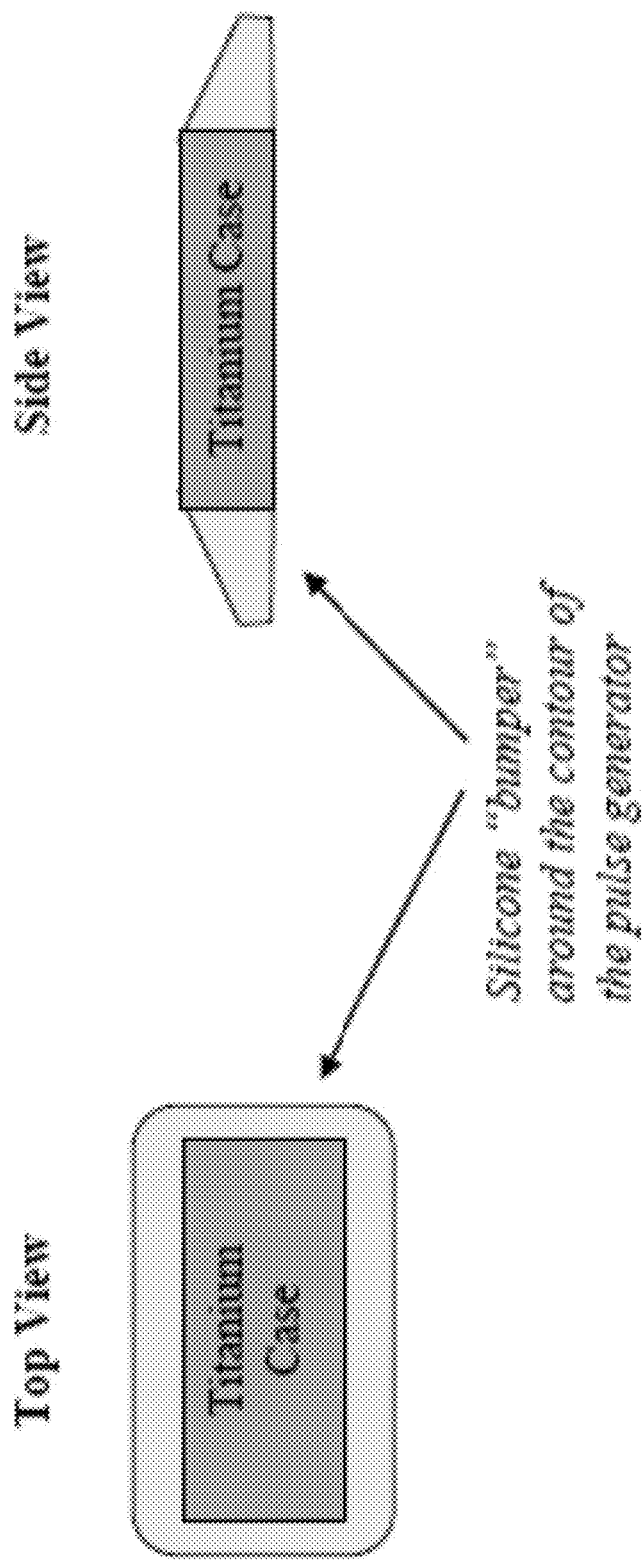
FIG. 9 illustrates top and side views of an example implantable pulse generator.

Soft Contour. The traditional material for an implantable medical device is Titanium. While Titanium may provide a stable hermetically sealed environment for the internal electronics, it is difficult to contour a Titanium case in an ergonomic manner. One embodiment would have the electronics encased in a Titanium can and surrounded by a softer material such a silicone to provide soft, tapered edges which maximize comfort and reduce associated skin tension as illustrated in FIG. 9. This soft contour can also be used to house the recharge coil in order to have the largest possible coil loop area for more efficient charging. Also by having the recharge coil outside and separate from the metallic enclosure helps reduce the heating and RF noise during recharging. Another embodiment is to encase the internal electronics in epoxy, glass or ceramics.

Figure 10:
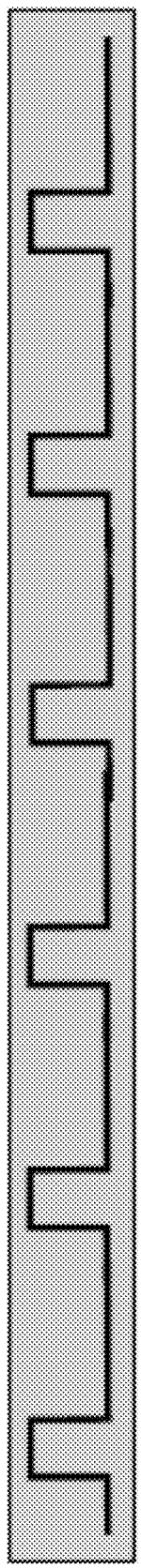
FIG. 10 illustrates an example electrical stimulation waveform for use in ONS for CM & ICM.

Electric Stimulation/Waveform. The electrical stimulation waveform generally used in ONS for CM & ICM is a traditional "Tonic" waveform which uses a repeating pattern of square pulses as illustrated in FIG. 10. This stimulation pattern is characterized by pulse amplitude, pulse width and stimulation frequency which are fixed parameters and do not evolve over time.

In recent years, newer advanced waveforms for SCS systems have been developed for the treatment of Chronic Pain. These waveforms can differ significantly from the tonic waveform and have demonstrated an increase in efficacy of pain relief as well as emotional and psychological benefits. The waveforms are described in greater detail in U.S. Pub. No. 2011/0184488 (hereinafter "Nevro"), entitled SPINAL CORD STIMULATION TO TREAT PAIN, and U.S. Pub. No. 2012/0016437 (hereinafter "BurstDR"), entitled SELECTIVE HIGH FREQUENCY SPINAL CORD MODULATION FOR INHIBITING PAIN WITH REDUCED SIDE EFFECTS, AND ASSOCIATED SYSTEMS AND METHODS, each of which is hereby incorporated by reference herein in its entirety.

Figure 11:
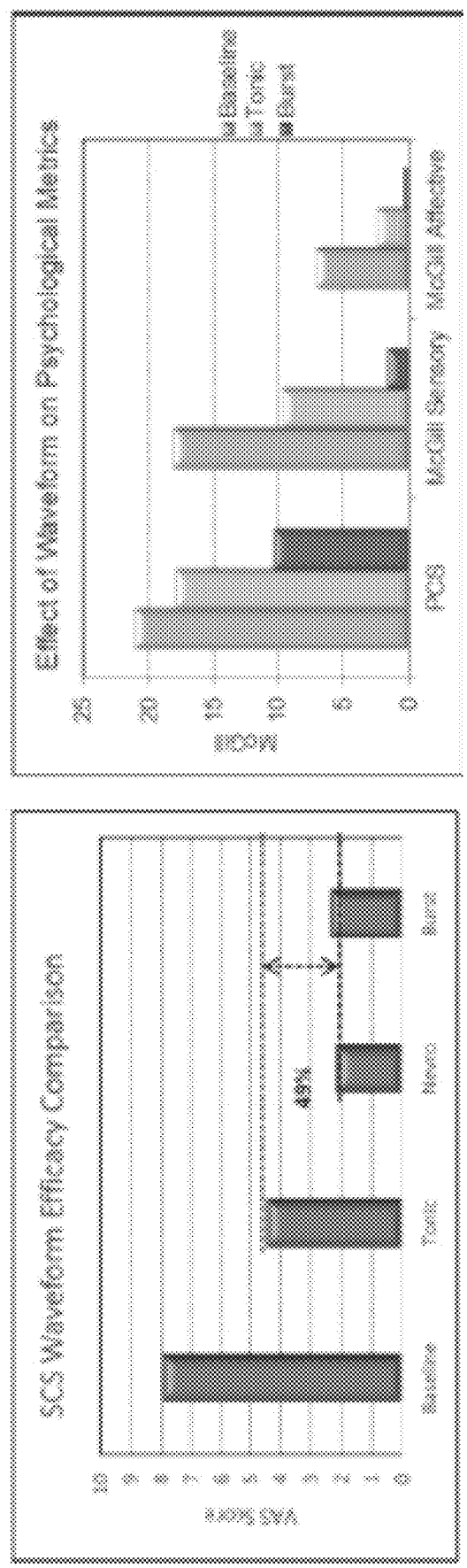
FIG. 11 illustrates comparative efficacy of tonic, Nevro HF10 and BurstDR waveforms for chronic pain.

In clinical studies, both advanced waveforms (for example, those described in Nevro, BurstDR) reduced the amplitude of the chronic pain in patients when compared to Tonic stimulation. This reduction in pain is evidenced by the reduction in VAS score which is a common pain assessment metric. It is noteworthy that Tonic stimulation significantly reduced VAS pain scores compared to Baseline and is considered an effective therapy, however, the advanced waveforms further reduced the VAS scores by approximately 49% compared to Tonic. In addition to the reduction of the VAS pain score, the BurstDR stimulation waveform also improved psychological metrics such as the Pain Catastrophizing Scale ("PCS") and the McGill Sensory and Affective scales indicating that the improvement associated with the advanced waveform provides benefits to the patient in multiple dimensions (FIG. 11).

The above referenced waveforms serve to illustrate the importance of the stimulation waveform in the ultimate efficacy of therapy. It is believed by the inventors and authors of this application that the efficacy of ONS for CM & ICM can be significantly increased by a waveform designed to counteract the phenomenon of adaptation as described earlier.

There are multiple parameters that control electrical stimulation of biologic tissue, such as, but not limited to, Amplitude, Pulse width, Frequency, Electrode configuration, Electrode polarity, Stimulation cycling with various on and off times, Recharge characteristics such as active/passive, and/or Pulse shape such as square or triangular (sloped).

Embodiments of the present disclosure provide systems and methods of modifying the stimulation waveform and parameters to increase the therapy efficacy and long term durability of ONS for CM & ICM (hereafter referred to as the "Waveforms"). These Waveforms may be used independently or in conjunction with one another. Additionally, they may be used at different times or under different conditions.

Embodiments of the present disclosure provide systems and methods of use for providing multiple Waveforms that may result in different benefits to the patient depending on the clinical context. It is therefore conceivable that certain Waveforms may be used in certain conditions and other Waveforms used in differing conditions. The implantable micro pulse generator may have the ability to change the Waveform automatically or by virtue of a command from the physician or patient. Depending on the physiological context which may be asserted by various means such as measuring a physiological parameter (nerve activity, blood pressure, etc.), one or more parameters of the Waveform may be changed. This change may also be performed for other reasons, such as but not limited to user input, time of day, periodicity, user activity level, a physiological parameter, or defined period of time.

WAVEFORMS. Embodiments of the present disclosure provide systems and methods for providing several novel waveforms detailed below. These waveforms may be used independently or in conjunction to one another.

Negative Decay Spike Train Stimulation.
Positive Increase Spike Train Stimulation.
Spike Train Repetition.
Spike Train Inversion.
Spike Train Relaxation.
Force Modulated Stimulation.
Multi-component Therapeutic Stimulation.

SPIKE TRAIN ADAPTATION. Considering the physiology and associated phenomenon illustrated in FIG. 3 and FIG. 4 where the firing frequency in sensory nerves naturally decays over time in spite of constant sensory stimulation, there are several "Spike Train Adaptation" inventions that could be beneficial for long-term efficacy of neurostimulation therapies.

Figure 12A:
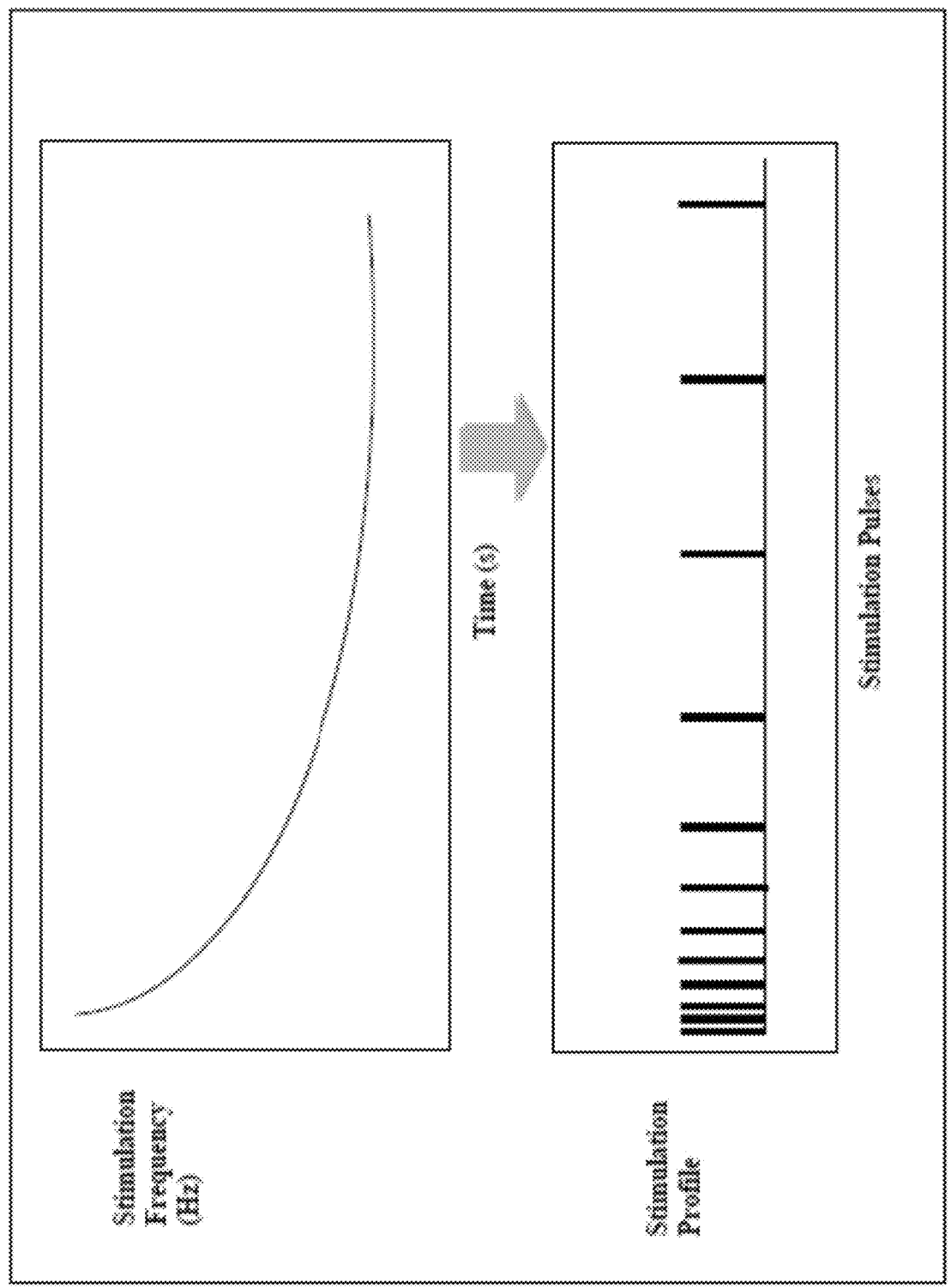
FIG. 12A illustrates example graphs corresponding to Negative Decay Spike Train Stimulation.

NEGATIVE DECAY SPIKE TRAIN STIMULATION. In this waveform modality, the inter-pulse frequency decays in a manner similar to the natural adaptation of sensory nerves. The premise is that a stimulation profile mimicking a natural firing pattern will not lead to central or cortical adaptation (FIG. 12A).

Figure 12B:
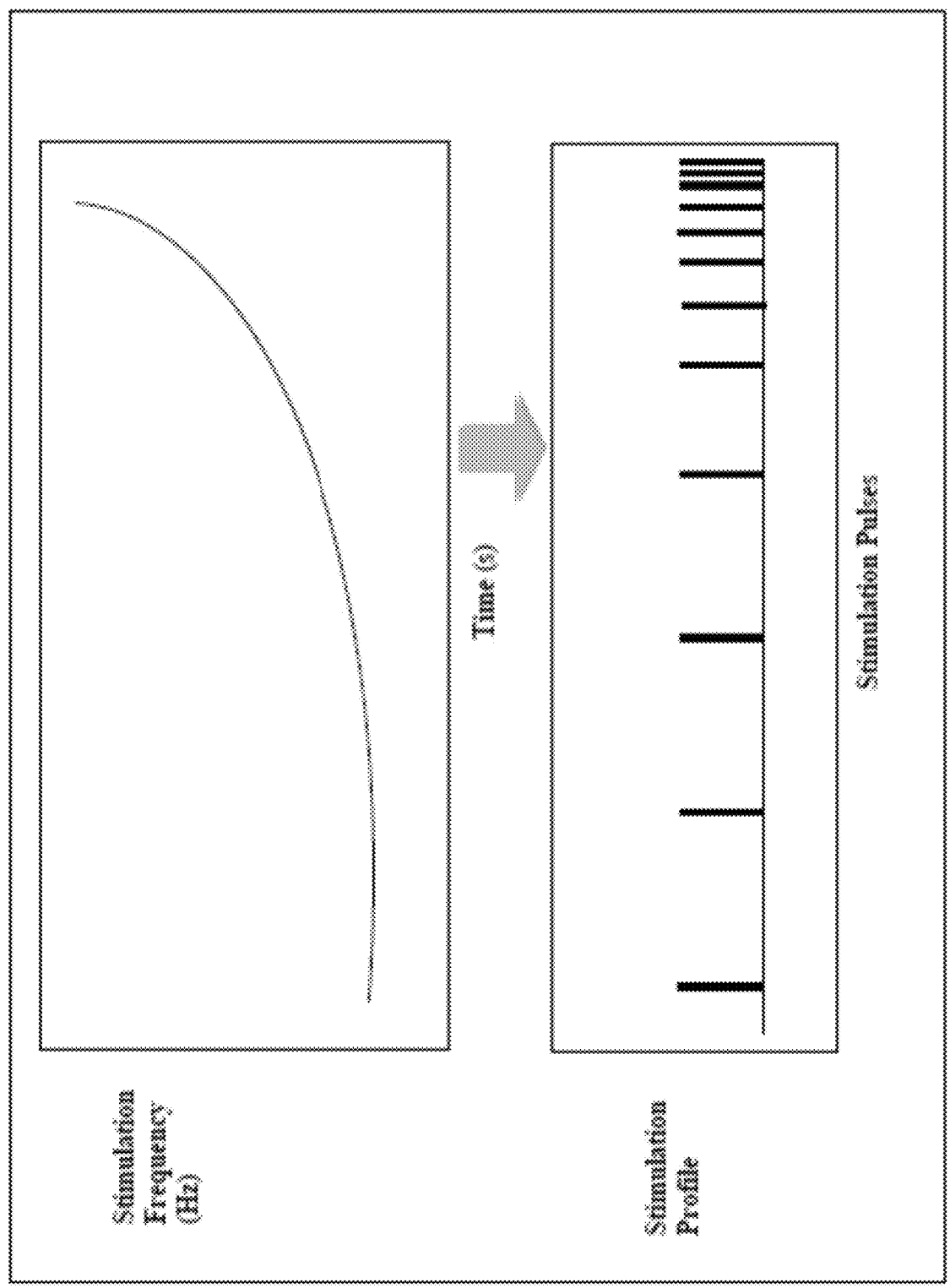
FIG. 12B illustrates example graphs corresponding to Positive Increase Spike Train Stimulation.

POSITIVE INCREASE SPIKE TRAIN STIMULATION. In this waveform modality, the inter-pulse frequency increases in a manner that is opposite to the natural adaptation of sensory nerves. The premise is that issuing stimulation pulses in at an increasing rate will overcome the natural tendency to adapt to the stimulation and thus increase therapeutic efficacy (FIG. 12B).

Figure 13A:
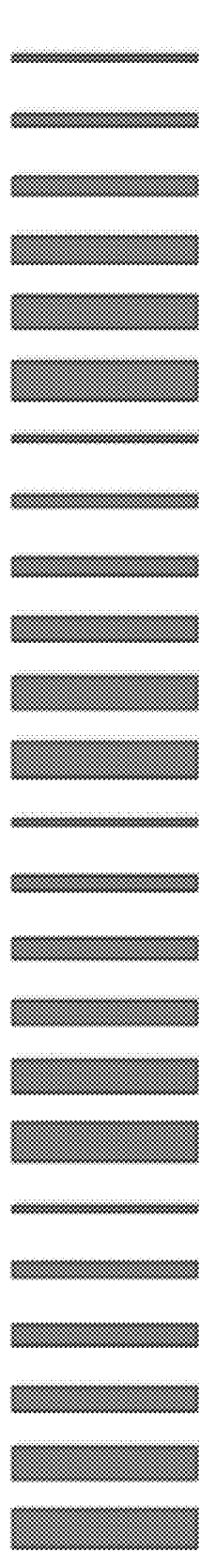
FIGS. 13A-I illustrate example Spike Train Stimulations.
Figure 13B:
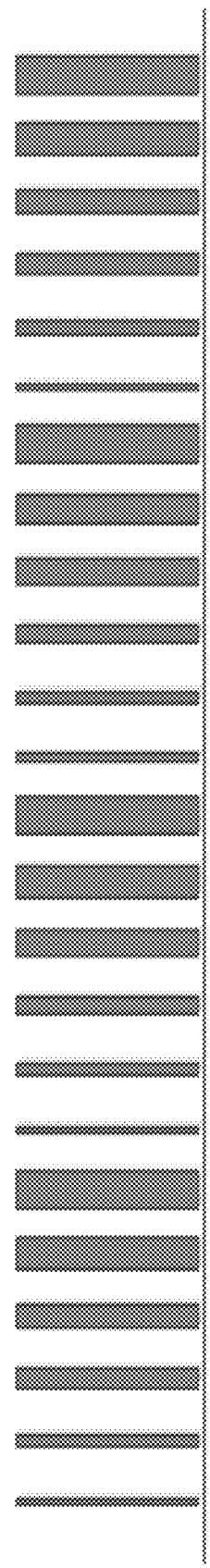
Figure 13C:

The previous embodiments describe Spike Train Stimulation relative to growth (increasing) or decay (decreasing) of the frequency in a linear fashion. Another embodiment of the Spike Train Stimulation is to have a waveform that grows or decays over time in a ramping fashion for other stimulation parameters such as amplitude or pulse width. FIG. 13A shows decaying pulse width in a linear fashion. FIG. 13B shows growing pulse width in a linear fashion. FIG. 13C shows alternating decaying and growing pulse width waveforms.

Figure 13D:
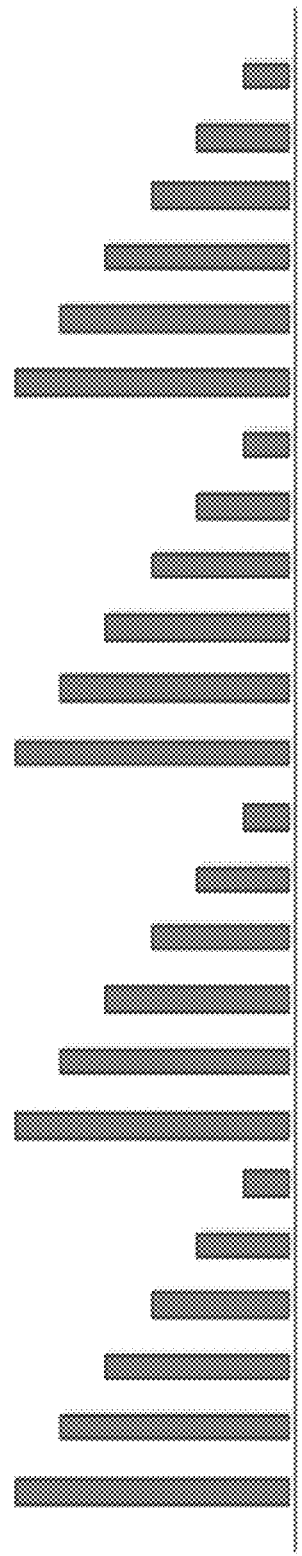
Figure 13E:
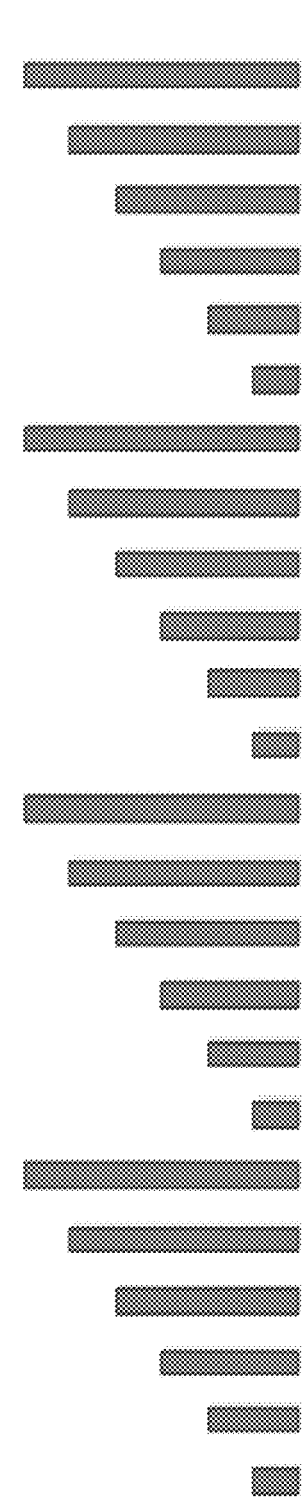
Figure 13F:
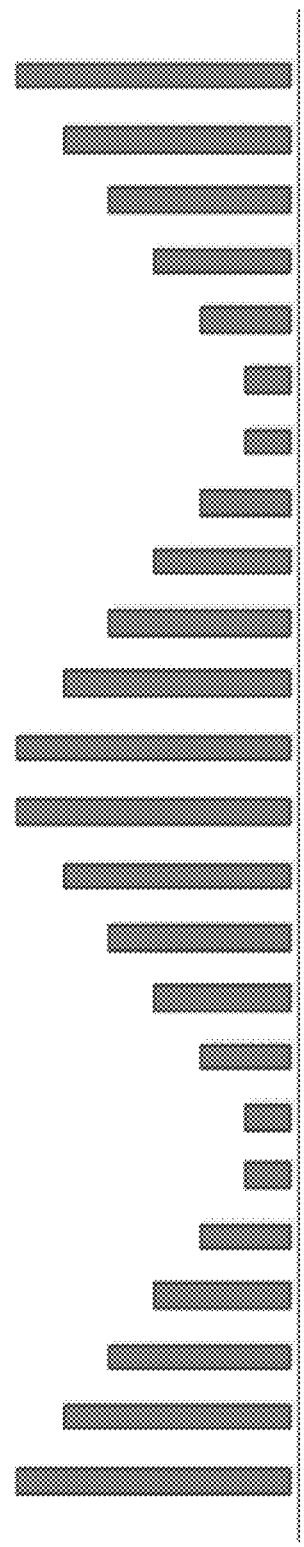

Similarly, the waveform can grow or decay over time in a ramping fashion where amplitude is the only variable parameter. FIG. 13D shows decaying amplitude, FIG. 13E shows growing amplitude and FIG. 13F shows decaying and growing amplitude in alternating fashion.

Figure 13G:
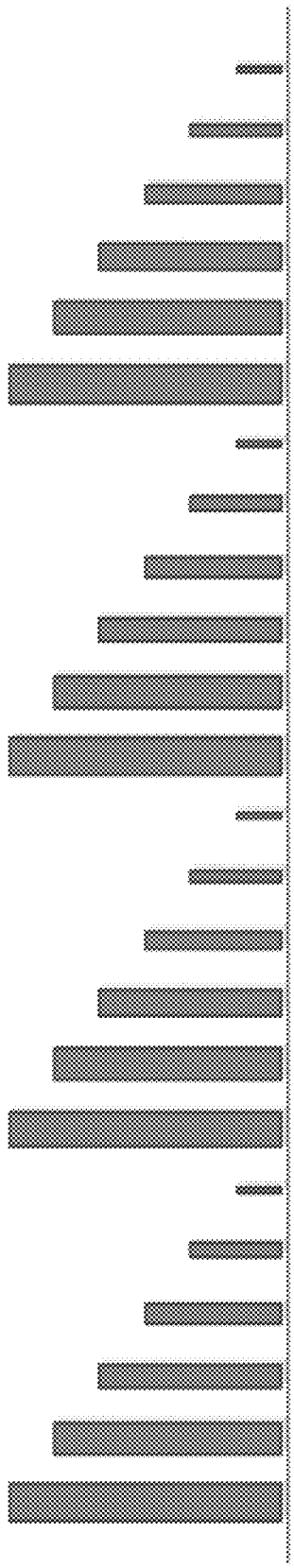
Figure 13H:
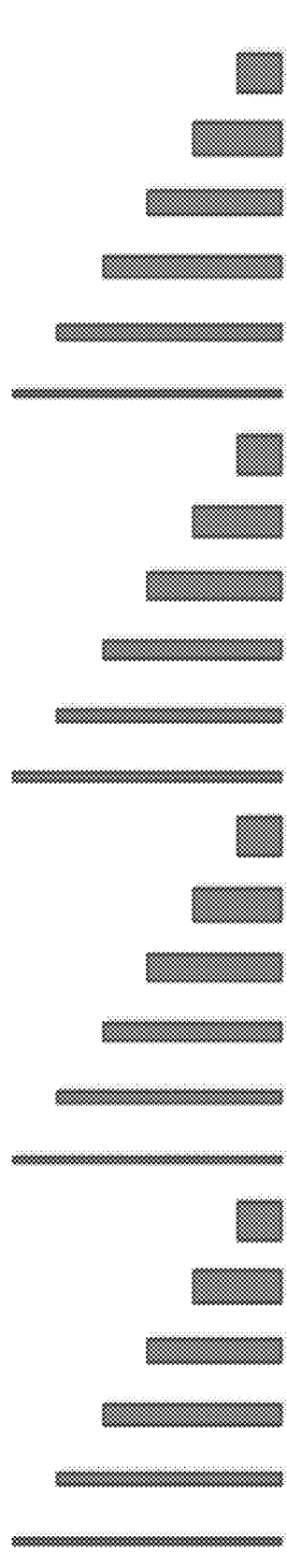
Figure 13I:
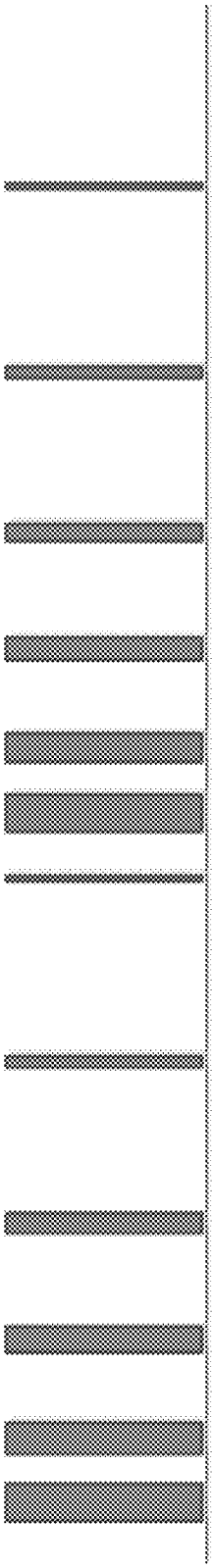

These parameters can be isolated to only parameter change as described above or they could be combined to create more complex signals. FIG. 13G illustrates a waveform with decaying pulse width and amplitude. FIG. 13H shows a waveform with a decaying amplitude and a growing pulse width. FIG. 13I shows a waveform with a growing frequency and decaying pulse width. There are many different combinations that can be created and all will not be detailed here.

Figure 14A:
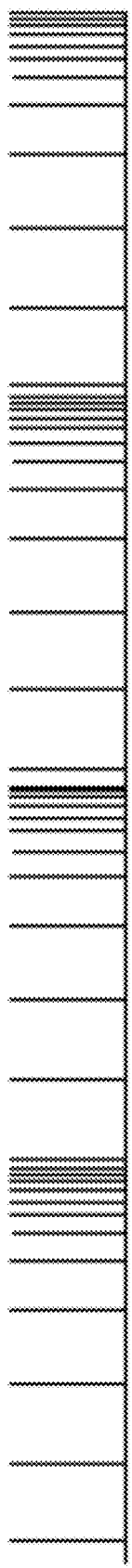
FIG. 14A illustrates an example of Positive Increase Spike Train Repetition.
Figure 14B:
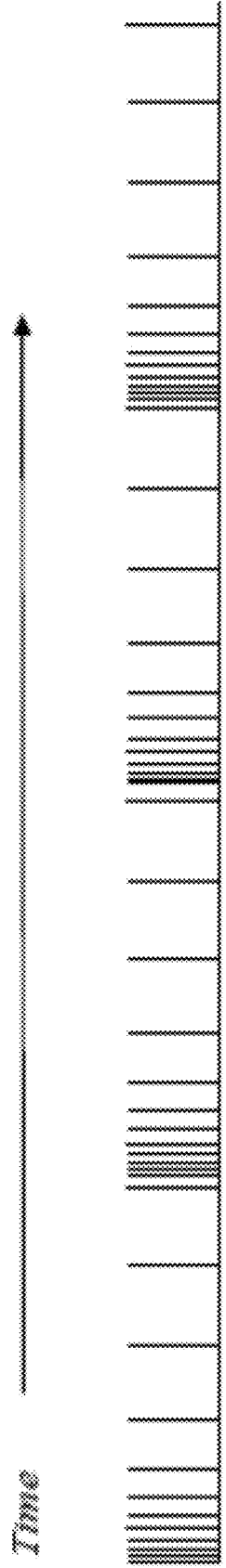
FIG. 14B illustrates an example of Negative Decay Spike Train Repetition.

SPIKE TRAIN REPETITION. As can be observed in FIG. 3 & FIG. 4, significant adaptation can occur in a matter of seconds. Therefore, the spike trains can have durations of approximately half a second to a minute (0.5 sec-60 sec). Once a spike train has completed, a new spike train is issued in a repetitive manner. One embodiment of the disclosure to overcome the adaption phenomenon is to stimulate the tissue with a positive increase spike train in repetitive fashion as illustrated in FIG. 14A. Another embodiment of the disclosure is to stimulate the tissue with a negative-decaying spike train in repetitive fashion as shown in FIG. 14B.

Figure 15:
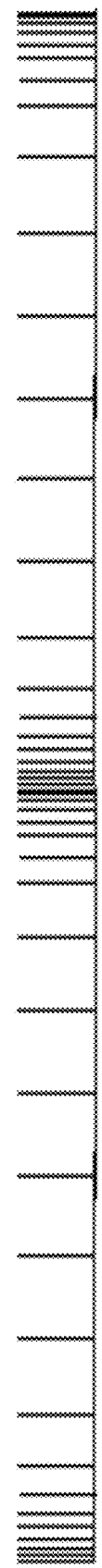
FIG. 15 illustrates an example of Spike Train Inversion.

SPIKE TRAIN INVERSION. In some instances, it may be desirable to invert the successive spike trains from positive to negative and vice-versa as illustrated in FIG. 15.

Figure 16:
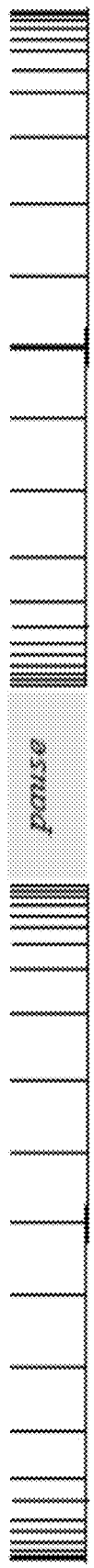
FIG. 16 illustrates an example of Spike Train Relaxation.

SPIKE TRAIN RELAXATION. As the spike trains will progressively activate the nerve and potentially trigger adaptation mechanisms, it may be desirable to add relaxation pauses between some of the spike trains. During these pauses, no stimulation pulses will be issued and the duration of the pauses will range approximately from 1 ms-60 seconds as shown in FIG. 16.

REGULARITY. It is noteworthy that the spike train waveforms are regular and deterministic in nature. There is no randomness or irregularity of the waveform.

REGULAR PHASE AMPLITUDE CLIPPING STIMULATION. In this waveform modality, a constant amplitude stimulation waveform is amplitude modulated by a regular, predetermine function such a Y=Sin(X) which is superimposed on the stimulation waveform and serves to determine the amplitude at each stimulation pulse (FIG. 17A).

Figure 17C:
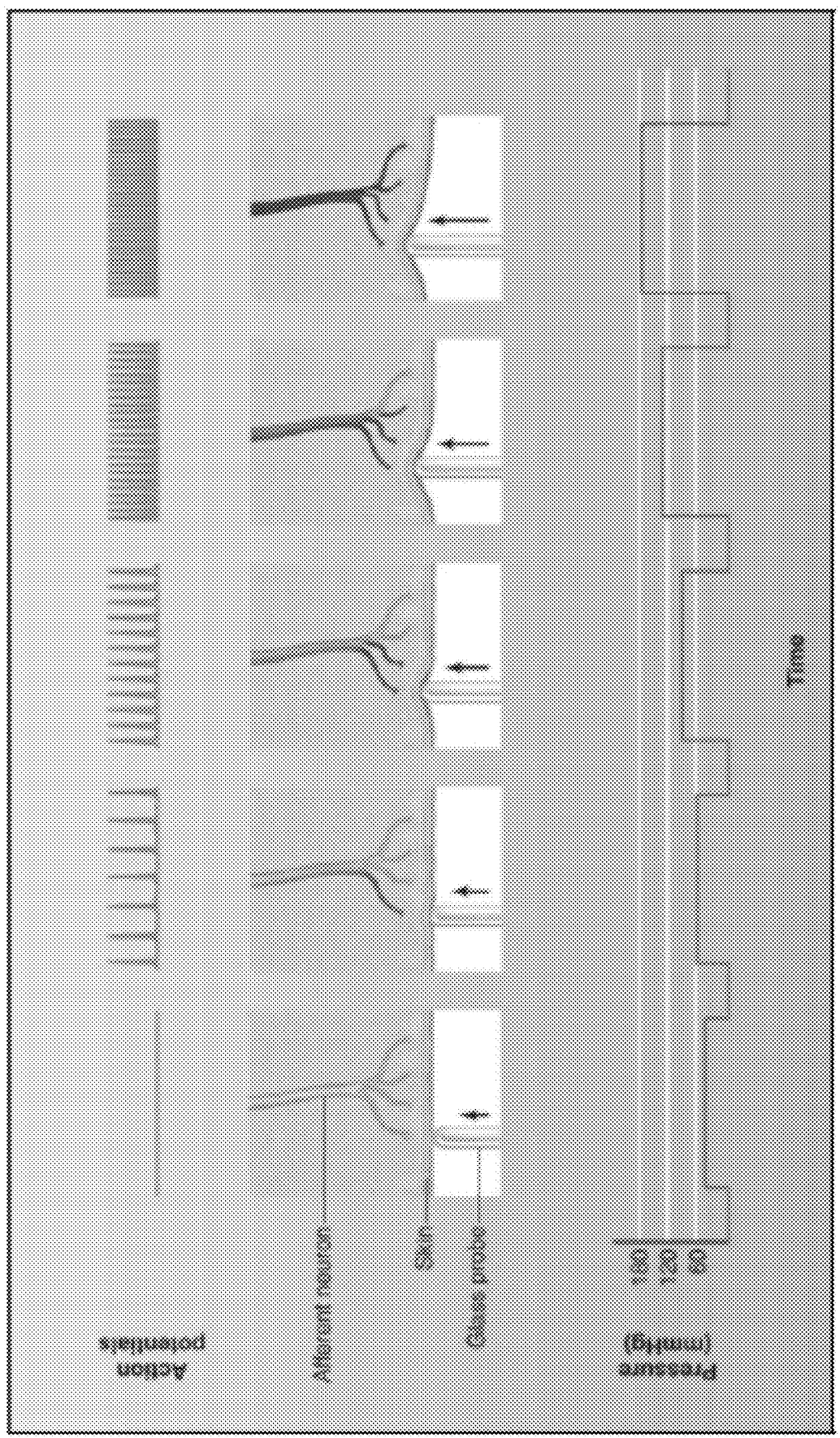
FIG. 17C illustrates an example of Afferent Neuron Action Potential Firing Frequency as Result of Increasing Pressure.

REGULAR PHASE WIDTH MODULATED STIMULATION. In this waveform modality, a constant amplitude stimulation waveform is width modulated by a regular, predetermine function such a Y=Sin(X) which is superimposed on the stimulation waveform and serves to determine the pulse width at each stimulation pulse (FIG. 17C).

FORCE MODULATED STIMULATION. The human body is continually exposed to mechanical forces such as motion, pressure, breathing, and heart beats. These forces are received by sensory nerves and their rate of firing constantly changes in response to the changing forces. FIG. 17C illustrates the increase in firing frequency of action potentials in a sensory afferent neuron in response to increase probe pressures on the skin. This phenomenon is experienced across the entire body and minute changes in posture, breathing, neck movement, all cause perpetual changes in the action potential firing frequency of afferent sensory neurons.

Figure 18:
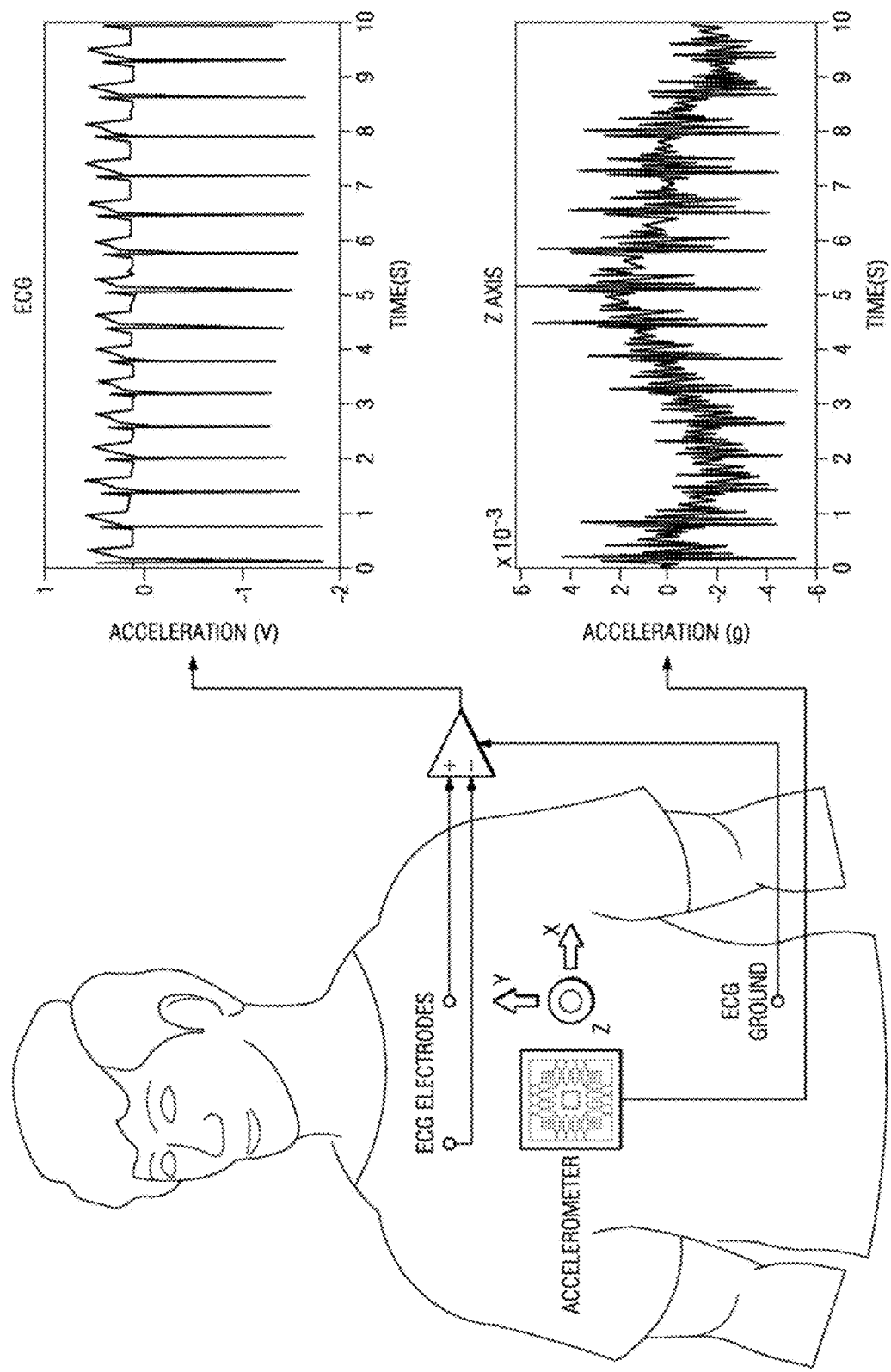
FIG. 18 illustrates example accelerometer signals displaying breathing and heartbeat information.

The mechanical forces to which the body is continually subject to, whether large or small, can be measured using an apparatus called an "accelerometer". The accelerometer is a relatively small electronic component which translates forces in one or multiples axis into electrical signals. The raw data from the accelerometer is then captured, read and processed by a microprocessor or a Digital Signal Processor (DSP). Accelerometers are widely used today to detect body position, activity, heartbeat and respiration rate. FIG. 18 illustrates the signal collected from the Z axis of an accelerometer placed on the chest of an individual. There are two major visible components in that signal. The "spikes" correlate to actual heartbeats, which is evidenced by the fact that they occur at the same time as the QRS complexes in the ECG. The slower sinusoidal drift of the baseline represents the motion of the chest in response to breathing. In this example, the X & Y axis data is not illustrated.

Figure 19:
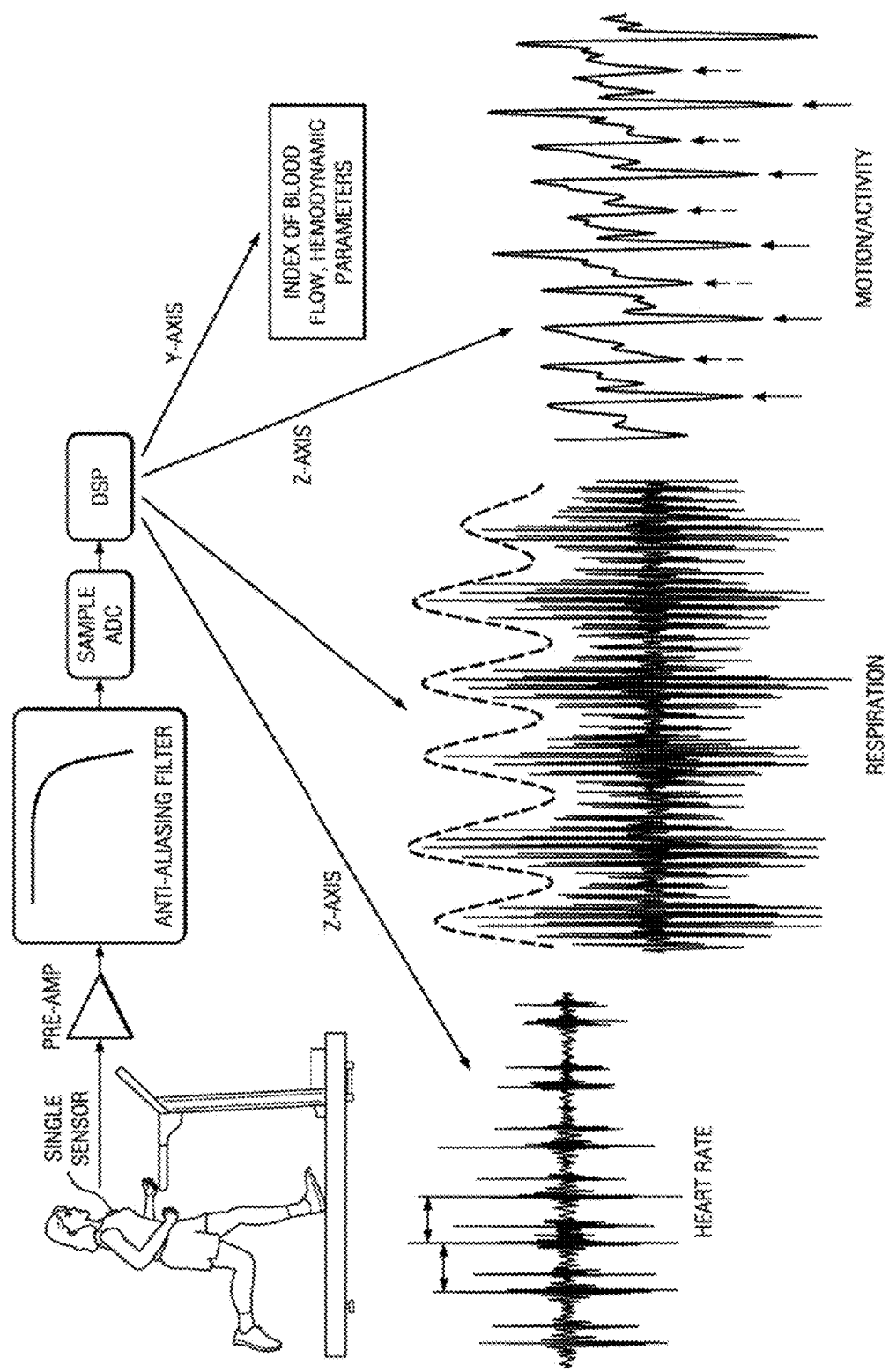
FIG. 19 illustrates example accelerometer signals displaying heartrate, breathing and forward motion.
Figure 22:
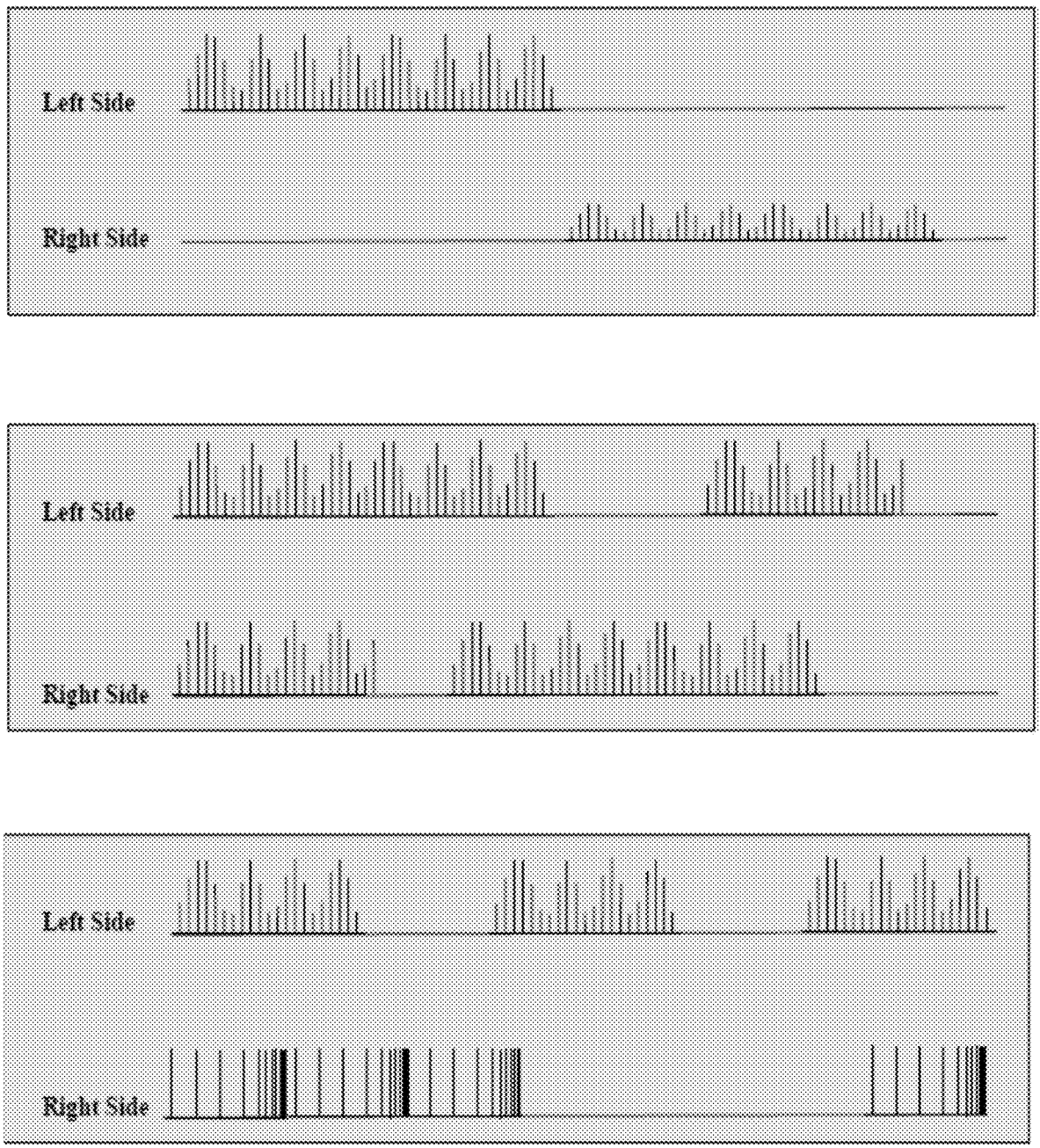
FIG. 22 illustrates example waveforms corresponding to independent lateral stimulation.

FIG. 19 illustrates a scenario where the accelerometer is placed on an individual's chest. The raw signal from the analog accelerometer is amplified, filtered and sampled via an analog to digital converter ("ADC") such as the one found on the Nordic nRF52 family chips. Note, certain accelerometers have the ADC embedded and therefore can communicate digitized signals; these are termed digital accelerometers. The sampled values are then processed by a DSP and physiological information such as heart rate, respiration and motion are extracted from signal.

It is customary to heavily filter and process the raw accelerometer signal in order to extract the signal of interest such as heartrate. However, in removing all of the other unwanted parts of the signal, one also removes minute but physiologically relevant information. These minute variations in the raw signal represent minute variations in forces to which the body is exposed and to which the nervous system responds by modulating the afferent firing frequency of sensory nerves. One embodiment of the present disclosure describes a method of using these unwanted or left over signals of the accelerometer signal to modulate the electrical stimulation pattern of the micro pulse generator for electrical stimulation therapy. More specifically, these left over signals could be used for ONS therapy to treat conditions such as CM & ICM by stimulating the target nerves which may perceive them as a naturally variable signal. These signals that are typically left over from the traditional use of an accelerometer can be used to either be the primary driver of the therapeutic stimulation or used to wobble around an already know therapeutic stimulation.

One embodiment of the present disclosure presents a method to capture the above described left over signals by considering a raw accelerometer signal where each axis is sampled in a 32 bit sample. The least significant bits ("LSB") of this sample represent minute variations in force and may be used to modulate the parameters of stimulation. It is additionally possible that multiple stimulation parameters may be modulated by different bit patterns in the sample. Yet another embodiment can utilize the LSBs of different accelerometer axis samples to modulate multiple stimulation parameters. The axis samples may also be mathematically combined to modulate one or more stimulation parameters.

Example: Accelerometer Modulated Stimulation Frequency

In another embodiment a pulse generator is programmed to deliver stimulation at a certain Base Frequency (F), Amplitude (A) and Pulse Width (PW) that contains a 3-axis digital accelerometer which produces unfiltered 32 bit samples for each axis at every sampling period. The pulse generator algorithm will sample the accelerometer X axis (X_SAMPLE) value at every stimulation pulse; once the current pulse is issued with (A, PW), a timer is set to determine the time for the next pulse. In tonic stimulation, this timer would be set to 1/F (the period). However, in one embodiment we set the timer value to: Timer=(1/F)+($-2^3$+X_SAMPLE[0 . . . 3]) where the timer value (period) will be between [1/F-8, 1/F+8] since we used the 4 least significant bits (LSB) of the X sample (bit0 . . . bit3). As previously discussed, the least significant bits of the raw unfiltered accelerometer sample contain minute but physiologically relevant information. In the above example, we extracted the 4 LSB's and used that value to modulate the stimulation frequency. The amplitude of the oscillation in frequency is bound from 0 to $2^4$ as no scaling factor was applied. The central frequency is the physician programmed base frequency (F). For example, if the physician programmed F=60 Hz, then at every pulse the accelerometer LSB's would cause the effective stimulation frequency to be between 52 Hz ($60-2^3$) and 68 Hz ($60+2^3$). This oscillation in frequency is providing a physiologically natural signal to the nervous system since afferent sensory fibers constantly change their firing frequency in response to minute changes in forces applied to the body.

There are numerous possible embodiments of this disclosure. The following possible embodiments are listed as examples and not meant to be limiting. Each example will be written in pseudo code that should be understood by one skilled in the art. The following information is useful to understanding the pseudocode:

Function IssuePulse is called by the pulse generator firmware every time a pulse is to be issued. The call to this function can be made from different locations in the IPG firmware, however it is common for this function to be called directly from the service routine of a hardware timer used to control the stimulation. The hardware timer will assert an interrupt at every (1/Frequency) time period.

ProgAmp is the base amplitude for stimulation programmed by the physician.

ProgPW is the base pulse width for stimulation programmed by the physician.

ProgElectrodes contains the information related to the selected electrodes to be used for stimulation by the physician. This may be an array of numbers indicating for each electrode whether it is OFF, ANODE or CATHODE.

Function SampleAccel retrieves a force sample from the accelerometer. This is a raw sample that is not filtered, averaged or modified in any way. This value may come directly from a digital accelerometer or from an ADC sampling an analog accelerometer. The argument passed to this function represents which axis of the accelerometer is to be sampled.

Function OutputPulse is used to cause a stimulation pulse to be issued by the output circuitry. For simplicity, we pass this function all of the necessary arguments required to issue this pulse: Amplitude, Pulse Width, and Electrode Configuration.

FreqDelta is a variable that will be used to control the frequency of the subsequent pulses. If this variable is set to zero, then the timers will be set according to the programmed frequency by the physician (ProgFreq). Otherwise the timers will be set according to ProgFreq+FreqDelta.

The X[0 . . . 3] notation in this pseudo-code indicates that the operation is to use the 4 least significant bits of X. The square brackets [ ] will be used for the purposed of extracting a set of contiguous bits from a larger word. Assume that X is a 32 bit unsigned integer, the ANSI C equivalent to A=X[0 . . . 3] would be:

A=X & 0x0000000F.

Here are several embodiments of various stimulation output routines written to utilize the data from the accelerometer in a way to modulate the output pulse:

Embodiment 1—Four LSBs From the X Axis of Accelerometer are Added "Wobble" to the Amplitude Output

```
Function IssuePulse (void)
{
    X = SampleAccel(X_AXIS);
    Amp = ProgrAmp + X[0..3];
    OutputPulse (Amp, ProgPW, ProgElectrodes);
}
```

Embodiment 2—Four LSBs From X Axis of Accelerometer are Added "Wobble" to the Amplitude Output and Four LSBs From the Y Axis are Added "Wobble" to the Pulse Width Output

```
Function IssuePulse
{
    X = SampleAccel(X_AXIS);
    Y = SampleAccel(Y_AXIS);
    Amp = ProgrAmp + X[0..3];
    PW = ProgPW - Y[0..1];
    OutputPulse (Amp, PW, ProgElectrodes);
}
```

Embodiment 3—Three LSBs From the X Axis and Three LSBs From the Z Axis of Accelerometer are Added "Wobble" to the Amplitude Output and Two LSBs From the Y Axis are Added "Wobble" to the Pulse Width Output

```
Function IssuePulse (void)
{
```

-continued

```
    X = SampleAccel(X_AXIS);
    Y = SampleAccel(Y_AXIS);
    Z = SampleAccel(Z_AXIS);
    Amp = ProgrAmp + X[0..2] + Z[0..2] << 2;
    PW = ProgPW − Y[0..1];
    OutputPulse (Amp, PW, ProgElectrodes);
}
```

Similarly, the "left over" signal from the accelerometer can be used to modulate other stimulation parameters such as Amplitude (Amp), Pulse Width (PW) and Frequency Delta (FreqDelta). These parameters are modified by using transform functions such as TransformAmp which implement any mathematical expression. The results of this transform are then scaled according to an arbitrary scaling factor. Finally, the scaled transformed values are range checked to make sure they are still within the bounds of safety and device performance envelope.

Embodiment 4—Sample Data Received From the Accelerometer is Used to Transform the Amplitude, Pulse Width and Frequency Based on a Desired Transform Mathematical Expression. In Addition, a Scaling Factor can be Added to Adjust the Impact of Modulation

```
Function IssuePulse(void)
{
    X = SampleAccel(X_AXIS);
    Y = SampleAccel(Y_AXIS);
    Z = SampleAccel(Z_AXIS);
    Amp = TransfromAmp(ProgrAmp , X) * ScalingFactorAmp;
    PW = TransfromPW(ProgrPW , Y) * ScalingFactorPW;
    FreqDelta = TransfromFreq(ProgFreq, , Z) * ScalingFactorFreq;
    RangeCheck (Amp, PW, FreqDelta);
    OutputPulse (Amp, PW, ProgElectrodes);
}
```

The above described functions are example embodiments of the present disclosure. It is also conceivable that other physiological metrics beyond motion such as EEG, ECG, Heart Rate Variability and natural signals such as sound, ambient temperature, atmospheric pressure could be used as an input signal to drive the modulation described above. For instance, the sample data from an EEG signal could be used in lieu of the sample data used from the accelerometer in the above example.

Similarly, there are synthetic signals such as music or harmonic sounds that could be used to primarily drive and/or complement therapeutic stimulation similar to the physiological or natural signals. For example, one embodiment could be using music as an input variable to determine the baseline parameter set, to provide the "wobble" in the primary stimulation parameter set or the mask to clip the desired waveform. A user could select their favorite song from their personal controller or inform the physician of their selection.

MULTICOMPONENT THERAPEUTIC STIMULATION. It is well known that the stimulation parameters used in ONS for CM & ICM affect the sensation perceived by the patient as well as the efficacy of therapy. One embodiment describes a method of combining stimulation parameters or Waveforms in order to combine the benefits of each individual parameter combination.

Assume a parameter set for ONS known to be efficacious at reducing headache frequency in a specific patient; for example Frequency 60 Hz, Amplitude 2 milli Amps and pulse width 450 micro seconds, let's call this Waveform1 in this example. Also assume a second waveform in the same patient which produces a pleasant massaging sensation, Frequency 11 Hz, Amplitude 0.5 milliAmps and pulse width of 750 micro seconds, let's call this Waveform 2 in this example. This disclosure proposes to superimpose both stimulation waveforms on the same stimulation channel simultaneously to provide both the therapeutic efficacy and pleasant massaging sensation to the patient. In isolation, the waveforms look like FIG. 20.

In order to provide the patient with the benefit of both waveforms, they will be superimposed by the micro pulse generator output circuitry and the patient will be stimulated with a hybrid waveform which is the sum of Waveform1 and Waveform2; this hybrid waveform will look similar to FIG. 21.

It is also expected that certain constraints may exist in the output circuitry of the micro pulse generator which may require some slight adjustments to the waveform in order to avoid pulse collisions, ineffective charge balancing and other technical considerations. These constraints will depend on the individual hardware however they are all anticipated in this disclosure. All of the parameters previously described in this disclosure can be modified for the purposes of meeting hardware constrains.

LATERAL COMPARTMENTALIZATION. Therapeutic stimulation of the Occipital Nerves for headache disorders such as CM and ICM, the same frequency is traditionally used on both the left and right occipital nerve network. There exists much asymmetry in the human body as well as in the presentation of CM & ICM in terms of the laterality of pain and shifting of pain patterns. In order to realize the maximum benefit of therapy, all parameters controlling stimulation should be independent between the left and right side stimulation because as the pain pattern shift so may the necessary therapeutic stimulation to provide efficacy.

INDEPENDENT LATERAL STIMULATION. ONS therapy for CM and ICM generally requires stimulation of the left and right occipital nerves. As previously described, an embodiment described in this disclosure is to have fully independent parameters sets for the left and right sided stimulation such as both sides can be independently optimized. In a first embodiment, the stimulation patterns on the left and right occipital nerves are occurring simultaneously. However, this may lead to high level habituation by the thalamus and may render therapy less effective over time. In order to defeat this habituation, the left and right sided stimulation may be alternated, such that the left side is being stimulated for a few seconds (Left Train) while the right side is quiescent; at the end of that stimulation period, the right side is stimulated (Right Train) while the left side is quiescent. This lateral alternation will cause a wobbling effect in the Thalamus preventing accommodation and habituation. In another embodiment there is an overlap between the left and right stimulation such that a blended effect will occur. In yet another embodiment, the left and right sided repeat frequencies are different such that their occurrence relative to one another or phase changes with time, further preventing accommodation and habituation (FIG. 23).

The concepts described in this application are compatible with and can be used in conjunction with any combination of the embodiments and/or features described in the following publications: (1) Carl Haub and Toshiko Kaneda, 2013 World Population Data Sheet; (2) Carod-Artal, Francisco Javier. "Tackling Chronic Migraine: Current Perspectives." Journal of Pain Research 7 (2014): 185-94. doi: 10.2147/JPR.S61819; (3) Schramm, Sara H., Mark Obermann, Zaza Katsarava, Hans-Christoph Diener, Susanne Moebus, and Min-Suk Yoon. "Epidemiological Profiles of Patients with Chronic Migraine and Chronic Tension-Type Headache." The Journal of Headache and Pain 14 (May 7, 2013): 40. doi: 10.1186/1129-2377-14-40; (4) Latinovic, R. "Headache and Migraine in Primary Care: Consultation, Prescription, and Referral Rates in a Large Population." Journal of Neurology, Neurosurgery & Psychiatry 77, no. 3 (Jul. 26, 2005): 385-87. doi: 10.1136/jnnp.2005.073221. (5) https://migraineresearchfoundation.org/about-migraine/migraine-facts; (6) Headache Classification Committee of the International Headache Society (IHS). "The International Classification of Headache Disorders, 3rd Edition (Beta Version)." Cephalalgia 33, no. 9 (Jul. 1, 2013): 629-808. doi: 10.1177/0333102413485658; (7) Menken, M., T. L. Munsat, and J. F. Toole. "The Global Burden of Disease Study: Implications for Neurology." Archives of Neurology 57. no. 3 (March 2000): 418-20; (8) Matharu, Manjit S. "BOTOX® (Botulinum Toxin Type A, BONTA, Allergan) in the Management of Chronic Migraine." Accessed Oct. 1, 2016. http://www.clusterheadacheinfo.org/local—files/file:botox-allergan/Botox_Allergan.pdf; (9) Silberstein, Stephen D., Richard B. Lipton, David W. Dodick, Frederick G. Freitag, Nabih Ramadan, Ninan Mathew, Jan L. Brandes, et al. "Efficacy and Safety of Topiramate for the Treatment of Chronic Migraine: A Randomized, Double-Blind, Placebo-Controlled Trial." Headache: The Journal of Head and Face Pain 47, no. 2 (February 2007): 170-80. doi: 10.1111/j.1526-4610.2006.00684.x; (10) Portfolio, Product, Access To Healthcare, Stay Up-to-Date, and Financial Data. "Novartis Announces AMG 334 Significantly Reduces Patients' Monthly Migraine Days in Phase II Study of Chronic Migraine Prevention." Accessed Oct. 2, 2016. https://www.novartis.com/news/media-releases/novartis-announces-amg-334-significantly-reduces-patients-monthly-migraine-days; (11) Silberstein, Stephen D., Anne H. Calhoun, Richard B. Lipton, Brian M. Grosberg, Roger K. Cady, Stefanie Dorlas, Kristy A. Simmons, et al. "Chronic Migraine Headache Prevention with Noninvasive Vagus Nerve Stimulation: The EVENT Study." Neurology 87, no. 5 (Aug. 2, 2016): 529-38. doi: 10.1212/WNL.0000000000002918; (12) Dodick, D. W., S. D. Silberstein, K. L. Reed, T. R. Deer, K. V. Slavin, B. Huh, A. D. Sharan, et al. "Safety and Efficacy of Peripheral Nerve Stimulation of the Occipital Nerves for the Management of Chronic Migraine: Long-Term Results from a Randomized, Multicenter, Double-Blinded, Controlled Study." Cephalalgia 35, no. 4 (Apr. 1, 2015): 344-58. doi: 10.1177/0333102414543331; (13) Saper, Joel R., David W. Dodick, Stephen D. Silberstein, Sally McCarville, Mark Sun, and Peter J. Goadsby. "Occipital Nerve Stimulation for the Treatment of Intractable Chronic Migraine Headache: ONSTIM Feasibility Study." Cephalalgia: An International Journal of Headache 31. no. 3 (February 2011): 271-85. doi: 10.1177/0333102410381142; (14) Miller, Sarah, Alex J. Sinclair, Brendan Davies, and Manjit Matharu. "Neurostimulation in the Treatment of Primary Headaches." Practical Neurology, 2016, practneurol-2015; (15) Bartsch, Goadsby & al. "Stimulation of the Greater Occipital Nerve Induces Increased Central Excitability of Dural Afferent Input." Brain 125, no. 7 (Jul. 1, 2002): 1496; (16) Magis, Jean Schoenen & al. "Central Modulation in Cluster Headache Patients Treated with Occipital Nerve Stimulation: An FDG-PET Study." BMC Neurology 11, no. 1 (2011): 1; (17) Matharu."Central Neuromodulation in Chronic Migraine Patients with Suboccipital Stimulators: A PET Study." Brain 127, no. 1 (Jan. 1, 2004): 220-30. doi: 10.1093/brain/awh022; (18) Vincent & al. Ottar Sjaastad. "Reduction of Calcitonin Gene-Related Peptide in Jugular Blood Following Electrical Stimulation of Rat Greater Occipital Nerve." Cephalalgia 12, no. 5 (1992); (19) Abbott, Regehr, "Synaptic Computation", Nature. 2004 Oct. 14; 431(7010):796-803; and/or (20) Matthews, B. H. C. 1931. The response of a single end organ. Journal of Physiology, 71, 64-110. Each of these publications is expressly bodily incorporated in its entirety and is part of this disclosure. Some or all of the features described herein can be used or otherwise combined together or with any of the features described in these publications.

APPLICABILITY AND GENERALIZATION OF INVENTIONS. This application presents examples in the context of ONS therapy for CM & ICM; this is meant to be illustrative and not limiting. The concepts of accommodation and habituation are omnipresent in all nervous tissue of the human body and non-nervous tissue as well. Thus, the described systems and method are applicable to a wide range of neurological disorders. For example, other applications can include, but are not limited to: Spinal Cord Stimulation for Chronic Pain, Deep Brain Stimulation for Movement Disorders, Vagus Nerve Stimulation for Epilepsy, Obesity and Inflammation, Tibial Nerve Stimulation for Incontinence, Pancreatic Stimulation for Diabetes, Cortical Stimulation for Epilepsy and Post Stroke Rehabilitation, Visceral Organ stimulation, Vascular stimulation, Muscle stimulation, and/or Other biological tissue responsive to the forms of stimulation listed below.

In addition, the stimulation profiles described within can be applied to many other means beyond electrical stimulation such as mechanical, ultrasonic, thermal, light, magnetic and electro-magnetic stimulation to evoke potentials in tissue.

Similarly, the hardware disclosures described in this application are related to an implantable pulse generator however it is conceivable these inventions could apply to devices that provide power transcutaneously to an implanted transceiver or that provide energy to the nerve structure entirely transcutaneously.

While certain embodiments of the inventions have been described, these embodiments have been presented by way of example only, and are not intended to limit the scope of the disclosure. Indeed, the novel methods and systems described herein may be embodied in a variety of other forms. Furthermore, various omissions, substitutions and changes in the systems and methods described herein may be made without departing from the spirit of the disclosure. Additionally, aspects, components, methods, features, advantages, and embodiments described herein can be combined with aspects, components, methods, features, advantages, and embodiments described in the publications and applications incorporated by reference here in.

Features, materials, characteristics, or groups described in conjunction with a particular aspect, embodiment, or example are to be understood to be applicable to any other aspect, embodiment or example described in this section or elsewhere in this specification unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

Furthermore, certain features that are described in this disclosure in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations, one or more features from a claimed combination can, in some cases, be excised from the combination, and the combination may be claimed as a subcombination or variation of a subcombination.

Moreover, while operations may be depicted in the drawings or described in the specification in a particular order, such operations need not be performed in the particular order shown or in sequential order, or that all operations be performed, to achieve desirable results. Other operations that are not depicted or described can be incorporated in the example methods and processes. For example, one or more additional operations can be performed before, after, simultaneously, or between any of the described operations. Further, the operations may be rearranged or reordered in other implementations. Those skilled in the art will appreciate that in some embodiments, the actual steps taken in the processes illustrated and/or disclosed may differ from those shown in the figures. Depending on the embodiment, certain of the steps described above may be removed, others may be added. Furthermore, the features and attributes of the specific embodiments disclosed above may be combined in different ways to form additional embodiments, all of which fall within the scope of the present disclosure. Also, the separation of various system components in the implementations described above should not be understood as requiring such separation in all implementations, and it should be understood that the described components and systems can generally be integrated together in a single product or packaged into multiple products.

For purposes of this disclosure, certain aspects, advantages, and novel features are described herein. Not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, or 0.1 degree.

The scope of the present disclosure is not intended to be limited by the specific disclosures of preferred embodiments in this section or elsewhere in this specification, and may be defined by claims as presented in this section or elsewhere in this specification or as presented in the future. The language of the claims is to be interpreted broadly based on the language employed in the claims and not limited to the examples described in the present specification or during the prosecution of the application, which examples are to be construed as non-exclusive.

What is claimed is:

1. A system for providing electrical stimulation to biological tissue to treat one or more medical conditions comprising:

one or more leads configured to be positioned proximate to biological tissue that is proximate one or more nerves;

a pulse generator configured to deliver electrical stimulation to the biological tissue via the one or more leads;

a power source configured to operatively connect and supply power to the pulse generator;

a motion sensor positioned proximate to a body of a patient and configured to generate a raw patient signal; and one or more processors configured to:
receive the raw patient signal from the motion sensor;
identify major variations and minor variations in the raw patient signal, wherein the major variations and minor variations correspond to one or more forces to which the body is exposed, wherein the major variations correspond to a signal of interest portion including physiologically significant information from the raw patient signal, and wherein the minor variations correspond to minute physiologically least significant information of an unwanted or left over signal portion of the raw patient signal;
periodically capture and extract insignificant data from minor variations that correspond to minute physiologically least significant information of the unwanted or left over signal portion of the raw patient signal unrelated to physiologically significant major variations of the signal of interest portion, wherein the insignificant data is limited to being extracted from portions corresponding to the minor variations, wherein the insignificant data is used to generate a stimulation signal by tuning a stimulation waveform according to the minor variations in the raw patient signal, and wherein the use of the insignificant data is unrelated to tailoring the stimulation based on the sensed physiologically significant major variations in the raw patient signal toward a predefined profile; and cause the pulse generator to deliver the electrical stimulation via the stimulation signal.

2. The system of claim 1, wherein the stimulation waveform comprises a series of pulses that vary in pulse width over time, wherein at least one of an inter-pulse frequency, a pulse amplitude, or the pulse width of the series of pulses increases over the time.

3. The system of claim 2, wherein the at least one of the inter-pulse frequency, the pulse amplitude, or the pulse width of the series of pulses increases linearly over the time.

4. The system of claim 2, wherein the at least one of the inter-pulse frequency, the pulse amplitude, or the pulse width of the series of pulses increases exponentially over the time.

5. The system of claim 2, wherein at least one of an inter-pulse frequency, a pulse amplitude, or the pulse width of the series of pulses decreases over the time.

6. The system of claim 5, wherein the at least one of the inter-pulse frequency, the pulse amplitude, or the pulse width of the series of pulses decreases linearly over the time.

7. The system of claim 5, wherein the at least one of the inter-pulse frequency, the pulse amplitude, or the pulse width of the series of pulses decreases exponentially over the time.

8. The system of claim 2, wherein at least one of an inter-pulse frequency, a pulse amplitude, or the pulse width of the series of pulses increases over the time, and wherein a different one of the at least one of the inter-pulse frequency, the pulse amplitude, or the pulse width of the series of pulses decreases over the time.

9. The system of claim 2, wherein the series of pulses is a first series of pulses over a first time period, and wherein the stimulation waveform comprises a second series of pulses over a second time period.

10. The system of claim 9, wherein a pattern of the second series of pulses matches a pattern of the first series of pulses.

11. The system of claim 9, wherein a pattern of the second series of pulses comprises an inverted pattern of a pattern of the first series of pulses.

12. The system of claim 2, wherein an inter-pulse frequency of the series of pulses varies over the time.

13. The system of claim 2, wherein an amplitude of the series of pulses varies over the time.

14. The system of claim 9, wherein the motion sensor is an accelerometer, wherein the stimulation waveform is characterized by a base frequency, amplitude, and pulse width, wherein tuning the stimulation waveform comprises modulating at least one of the base frequency, amplitude, or pulse width based on the minor variations in the raw patient signal.

15. The system of claim 1, wherein the one or more processors is further configured to further tune the stimulation signal based at least in part on at least one of user input, a time of day, a user activity level, a physiological parameter, or a predetermined pattern.

16. The system of claim 1, wherein the stimulation waveform is adapted to reduce an effect of neural accommodation or adaptation.

17. A method for providing electrical stimulation to biological tissue to treat medical conditions, the method comprising:

receiving a raw patient signal from a motion sensor, wherein the motion sensor is positioned proximate to a body of a patient;

identifying major variations and minor variations in the raw patient signal, wherein the major variations and minor variations correspond to one or more forces to which the body is exposed, wherein the major variations correspond to a signal of interest portion including physiologically significant information from the raw patient signal, and wherein the minor variations correspond to minute physiologically least significant information of an unwanted or left over signal portion of the raw patient signal;

periodically capturing and extracting insignificant data from minor variations that correspond to minute physiologically least significant information of the unwanted or left over signal portion of the raw patient signal unrelated to physiologically significant major variations of the signal of interest portion, wherein the insignificant data is limited to being extracted from portions corresponding to the minor variations, wherein the insignificant data is used to generate a stimulation signal by tuning a stimulation waveform according to the minor variations in the raw patient signal, and wherein the use of the insignificant data is unrelated to tailoring the stimulation based on the sensed physiologically significant major variations in the raw patient signal toward a predefined profile; and causing a pulse generator to deliver electrical stimulation to biological tissue that is proximate one or more nerves, wherein to deliver the electrical stimulation, one or more processors causes the pulse generator to apply the stimulation signal via one or more leads positioned proximate to the biological tissue.

18. The method of claim 17, wherein the stimulation waveform comprises a series of pulses, and wherein pulse width of the series of pulses varies over time, wherein at least one of an inter-pulse frequency, a pulse amplitude, or the pulse width of the series of pulses increases over the time, and wherein a different one of the inter-pulse frequency, the pulse amplitude, or the pulse width of the series of pulses decreases over the time.

19. The method of claim 18, wherein the stimulation waveform comprises one or more relaxation pauses between at least some of the series of pulses.

20. The method of claim 18, wherein an inter-pulse frequency of the series of pulses varies over the time.

21. The method of claim 18, wherein an amplitude of the series of pulses varies over the time.

22. The method of claim 18, wherein the stimulation waveform is adapted to reduce an effect of neural accommodation or adaptation.

* * * * *